(12) United States Patent
Gion et al.

(10) Patent No.: US 8,410,259 B2
(45) Date of Patent: *Apr. 2, 2013

(54) RECOMBINANT EXPRESSION VECTOR ELEMENTS (REVES) FOR ENHANCING EXPRESSION OF RECOMBINANT PROTEINS IN HOST CELLS

(75) Inventors: Wendy R. Gion, Charlton, MA (US); Gerald R. Carson, Belmont, MA (US); Hong Gao, Allston, MA (US); Yune Z. Kunes, Winchester, MA (US)

(73) Assignee: AbbVie Inc., North Chicago, IL (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/098,337

(22) Filed: Apr. 29, 2011

(65) Prior Publication Data

US 2011/0201053 A1 Aug. 18, 2011

Related U.S. Application Data

(63) Continuation of application No. 12/079,748, filed on Mar. 28, 2008, now Pat. No. 7,935,808.

(60) Provisional application No. 60/921,141, filed on Mar. 30, 2007.

(51) Int. Cl.
*C07H 21/04* (2006.01)
*C12N 15/74* (2006.01)

(52) U.S. Cl. ............... 536/24.1; 536/23.1; 424/93.2; 424/93.21; 435/320.1

(58) Field of Classification Search .................. None
See application file for complete search history.

(56) References Cited

U.S. PATENT DOCUMENTS

| | | | |
|---|---|---|---|
| 6,027,915 A | 2/2000 | Morris et al. | |
| 6,309,841 B1 | 10/2001 | Morris et al. | |
| 6,312,951 B1 | 11/2001 | Morris et al. | |
| 6,596,514 B2 | 7/2003 | Morris et al. | |
| 7,129,062 B2 | 10/2006 | Mermod et al. | |
| 7,935,808 B2 * | 5/2011 | Gion et al. | ........... 536/24.1 |
| 2008/0171014 A1 | 7/2008 | Wu et al. | |

FOREIGN PATENT DOCUMENTS

| | | |
|---|---|---|
| EP | 0 873 405 BI | 9/2004 |
| WO | WO 90/05144 A1 | 5/1990 |
| WO | WO 97/25420 A1 | 7/1997 |
| WO | WO 2004/033693 A1 | 4/2004 |
| WO | WO 2005/047512 A2 | 5/2005 |
| WO | WO 2007/024715 A2 | 3/2007 |

OTHER PUBLICATIONS

Bird et al., "Single-Chain Antigen-Binding Proteins," *Science*, 242: 423-426 (1988).
Bode et al., "Scaffold/Matrix-Attached Regions: Structural Properties Creating Transcriptionally Active Loci," *Int. Rev. Cytol.*, 162A: 389-454 (1995).
Bode et al., "Scaffold/Matrix-Attached Regions: Topological Switches with Multiple Regulatory Functions," *Crit. Rev. Eukaryotic Gene Expression*, 6(2 &3): 115-138 (1996).
Chattopadhyay et al., Chapter 10, "MARs and MARBPs, Key Modulators of gene regulation and disease manifestation," in *Subcellular Biochemistry*, vol. 41 (Kundu and Dasgupta, eds.) (Springer, 2007) pp. 213-230.
Dillon et al., "Transcriptional regulation of multigene loci: multilevel control," *Trends Genet.*, 9(4): 134-137 (1993).
Durocher et al., "High-level and high-throughput recombinant protein production by transient transfection of suspension-growing human 293-EBNA1 cells," *Nucl. Acids Res.*, 30(2e9): 1-9 (2002).
Grosveld et al., "Position-Independent, High-Level Expression of the Human β-Globin Gene in Transgenic Mice," *Cell*, 51: 975-985 (1987).
Holliger et al., "'Diabodies': Small bivalent and bispecific antibody fragments," *Proc. Natl. Acad. Sci. USA*, 90: 6444-6448 (1993).
Huston et al., "Protein engineering of antibody binding sites: Recovery of specific activity in an anti-digoxin single-chain Fv analogue produced in *Escherichia coli*," *Proc. Natl. Acad. Sci USA*, 85: 5879-5883 (1988).
Kaufman et al., "Coamplification and Coexpression of Human Tissue-Type Plasminogen Activator and Murine Dihydrofolate Reductase Sequences in Chinese Hamster Ovary Cells," *Mol. Cell. Biol.*, 5(7): 1750-1759 (1985).
Kaufman, R.J., "High Level Production of Proteins in Mammalian Cells," in *Genetic Engineering: Principles and Methods*, vol. 9, (Setlow, J.K., ed.) (Plenum Publishing, New York, 1987) pp. 155-198.
Kaufman, R.J., "Selection and Coamplification of Heterologous Genes in Mammalian Cells," *Methods Enzymol.*, 185: 537-566 (1990).
Kellum et al., "A Position-Effect Assay for Boundaries of Higher Order Chromosomal Domains," *Cell*, 64: 941-950 (1991).
McBratney et al., "Internal initiation of translation," *Curr. Opin. Cell Biol.*, 5: 961-965 (1993).
Michalowski et al., "Characterization of Randomly-Obtained Matrix Attachment Regions (MARs) from Higher Plants," *Biochemistry*, 38: 12795-12804 (1999).
Needleman et al., "A General Method Applicable to the Search for Similarities in the Amino Acid Sequence of Two Proteins," *J. Mol. Biol.*, 48: 443-453 (1970).
Nelson et al., "Characterization of a Human Locus in Transition," *J. Biol. Chem.*, 269(49): 31067-31073 (1994).
Poljak, R.J., "Production and structure of diabodies," *Structure*, 2: 1121-1123 (1994).
Reynaud et al., "The Size of the Transcriptional Units of the Avian Globin Genes Defined at the Pre-messenger RNA Level," *J. Mol. Biol.*, 140: 481-504 (1980).
Sumer et al., "A Rapid Method of Genomic Array Analysis of Scaffold/Matrix Attachment Regions (S/MARs) Identifies a 2.5-Mb Region of Enhanced Scaffold/Matrix Attachment at a Human Neocentromere," *Genome Res.*, 13: 1737-1743 (2003).
Tikhonov et al., "Structural Domains and Matrix Attachment Regions along Colinear Chromosomal Segments of Maize and Sorghum," *The Plant Cell*, 12: 249-264 (2000).

(Continued)

*Primary Examiner* — Q. Janice Li
(74) *Attorney, Agent, or Firm* — Stephen J. Gaudet; Thomas R. Berka; Yankwich & Associates, P.C.

(57) ABSTRACT

Compositions and methods comprising recombinant expression vector elements (rEVEs) to enhance the level of expression of recombinant proteins are described. Other compositions and methods for lowering, substantially suppressing, or essentially silencing expression of a recombinant protein are also described.

12 Claims, 9 Drawing Sheets

OTHER PUBLICATIONS

Urlaub et al., "Isolation of Chinese hamster cell mutants deficient in dihydrofolate reductase activity," *Proc. Natl. Acad. Sci. USA*, 77: 4216-4220 (1980).

Ward et al., "Binding activities of a repertoire of single immunoglobulin variable domains secreted from *Escheria coli*," *Nature*, 341: 544-546 (1989).

Zhong et al., "Flanking nuclear matrix attachment regions synergize with the T cell receptor δ enhancer to promote V(D)J recombination," *Proc. Natl. Acad. Sci. USA*, 96(21): 11970-11975 (1999).

Zhou et al., "Identification and characterization of a silkgland-related matrix association region in *Bombyx mori*," *Gene*, 277: 139-144 (2001).

Barnes et al., "Mammalian cell factories for efficient and stable protein expression," Curr. Opin. Biotechnol. 17: 381-386 (2006).

Harraghy et al., "Sustained transgene expression using MAR elements," Curr. Gene Therapy, 8: 353-366 (2008).

Jiang, Zhou et al., "Regulation of recombinant monoclonal antibody production in Chinese hamster ovary cells: A comparative study of gene copy number, mRNA level, and protein expression," Biotechnol. Prog., 22: 313-318 (2006).

Katakura, Yoshinori et al., "Productivity enhancement of recombinant protein in CHO cells via specific promoter activation by oncogenes," Cytotechnology, 31: 103-109 (1999).

Kim, Jong-Mook et al., "Improved recombinant gene expression in CHO cells using matrix attachment regions," J. Biotech., 107: 95-105 (2004).

Kwaks et al., "Employing epigenetics to augment the expression of therapeutic proteins in mammalian cells," Trends Biotechnol., 24: 137-142 (2006).

Lee, Suk Kyoo et al., "Development of apoptosis-resistant dihydrofolate reductase-deficient Chinese hamster ovary cell line," Biotechnol. Bioeng. 82: 872-876 (2003).

Lucas et al., "High-level production of recombinant proteins in CHO cells using a dicistronic DHFR intron expression vector," Nucl. Acids Res., 24: 1774-1779 (1996).

Zahn-Zabal et al., "Development of stable cell lines for production or regulated expression using matrix attachment regions," J. Biotech. 87: 29-42 (2001).

Extended European Search Report, dated Oct. 29, 2010, for European patent application No. 08727191.2.

International Search Report and Written Opinion, issued Sep. 22, 2008, for international application No. PCT/US2008/004063 (with attached Gene Bank sequence search summary, Aug. 28, 2008).

International Preliminary Report on Patentability (Chapter II), issued Nov. 23, 2010, for international application No. PCT/US2008/004063.

Forrester et al., "Nuclear matrix attachment regions antagonize methylation-dependent repression of long-range enhancer-promoter interactions," Genes. Dev., 13: 3003-3014 (1999).

Lutzko et al., "Lentivirus Vectors Incorporating the Immunoglobulin Heavy Chain Enhancer and Matrix Attachment Regions Provide Position-Independent Expression in B Lumphocytes," J. Virol., 77: 7341-7351 (2003).

\* cited by examiner

RECOMBINANT EXPRESSION VECTOR ELEMENTS (REVES) FOR ENHANCING EXPRESSION OF RECOMBINANT PROTEINS IN HOST CELLS

CROSS-REFERENCE TO RELATED APPLICATIONS

This application is a continuation of U.S. Ser. No. 12/079,748, filed Mar. 28, 2008 (now U.S. Pat. No. 7,935,808), which claims the benefit of priority to U.S. provisional application No. 60/921,141, filed Mar. 30, 2007.

BACKGROUND

A variety of systems are available that employ nucleic acid vector molecules for the expression of recombinant proteins in a diverse and wide variety of eukaryotic or prokaryotic host cells. The decision of which vector/host cell pair to use typically depends upon which system provides the highest yield of the desired recombinant gene product in a form best suited for its intended use. For example, if a post-translational modification, such as glycosylation, is critical to requirements of the desired recombinant protein (e.g., for antigenicity, activity, conformation, etc.), then a eukaryotic host cell system will be desired as prokaryotic cells are characteristically devoid of post-translational glycosylation activity. It is also important that a vector/host cell pair not only produce an expressed gene product in the desired form, but also that molecules of the desired expressed gene product can be readily isolated from the cells that produce them.

Owing to the escalating costs involved in the development of recombinant proteins intended for human therapy, there remains an ongoing effort to enhance the level of expression of such recombinant proteins, especially in systems that employ eukaryotic host cells. Various cis- and trans-acting regulatory elements have been characterized that have nucleotide sequences (DNA or RNA) that may improve efficiency of expression and/or overall yield of the desired recombinant gene product. Such regulatory elements include, but are not limited to, highly efficient promoters, transcriptional enhancer sequences (see, e.g., the review by Dillon and Grosveld, *Trends Genet.,* 9: 134 (1993), locus control regions (LCRs; see, e.g., Grosveld et al., *Cell,* 51: 975 (1987)), matrix or scaffold attachment regions (MARs, SARs; see, e.g., U.S. Pat. No. 7,129,062; Bode et al., *Int. Rev. Cytol.,* 162A: 389-454 (1995); Bode et al., *Crit. Rev. Eukaryotic Gene Expression,* 6: 115-138 (1996)); insulator elements (see, e.g., Kellum et al., *Cell,* 64: 941 (1991); and internal ribosome entry sites (IRES; see, e.g., review by McBratney et al., *Curr. Opin. Cell Biol.,* 5: 961 (1993)). Some of the nucleic acid sequences of such elements have been subsequently found to possess specific subsequences that can affect expression.

Despite advances in the understanding of various sequences and other factors that can affect expression of recombinant proteins in various types of host cells, needs remain to improve the yields of recombinant proteins, particularly when such recombinant proteins are intended for therapeutic or other specialized applications.

SUMMARY OF THE INVENTION

The present invention provides isolated nucleic acid molecules (polynucleotide molecules) comprising nucleotide base sequences that enhance expression of recombinant proteins. Such nucleic acid molecules are referred to herein as recombinant expression vector elements (rEVEs). The presence of a rEVE on an expression vector enhances the level of expression of one or more recombinant proteins encoded by one or more functional genes that reside on the expression vector as compared to the level of expression in the absence of the rEVE. Such rEVE-mediated enhancement of the level of expression of a recombinant protein is possible whether a rEVE is located 5' to, 3' to, or both 5' and 3' to (e.g., flanking) a gene encoding a recombinant protein(s) of interest. A rEVE present on an expression vector may enhance expression of one or more recombinant proteins whether encoded on separate corresponding genes or encoded on a single polycistronic gene present on the expression vector. REVEs may be used to enhance the level of expression of a recombinant protein using both stable expression systems and transient expression systems.

In one embodiment, the invention provides an isolated rEVE polynucleotide molecule that comprises a nucleotide base sequence selected from the group consisting of the sequence of bases of SEQ ID NO:1 ("ARM1"), the sequence of bases of SEQ ID NO:2 ("ARM2"), and an expression enhancing portion of any of the preceding sequences, wherein when the rEVE polynucleotide is present on the same expression vector as a recombinant gene encoding a recombinant protein of interest, the level of expression of the recombinant protein will be enhanced compared to the level of expression in the absence of the rEVE.

Preferred rEVE molecules of the invention include a 2329 base pair (bp) rEVE nucleic acid molecule that has the nucleotide base sequence of SEQ ID NO:1 and a 2422 by rEVE nucleic acid molecule that has the nucleotide base sequence of SEQ ID NO:2.

The 3' terminal region of the sequence of SEQ ID NO:2 contains sequences that are critical for rEVE-mediated enhancement of protein expression. Such preferred 3' terminal region sequences of SEQ ID NO:2 include the sequence of bases 462-2422 of SEQ ID NO:2 and the sequence of bases 1087-2422 of SEQ ID NO:2.

An isolated rEVE nucleic acid molecule comprising one or more of the nucleotide base sequences described herein may have any of a variety of forms including, without limitation, a linear nucleic acid molecule, a plasmid, a eukaryotic viral molecule, a prokaryotic viral (bacteriophage) molecule, an artificial chromosome, and a recombinant chromosome.

In a preferred embodiment, the invention provides an expression vector comprising at least one rEVE described herein. Such a rEVE-containing expression vector provides enhanced (elevated) levels of expression in an appropriate host cell of at least one recombinant protein encoded on the expression vector compared to the level of expression in the host cell carrying the same expression vector lacking the rEVE. Expression vectors useful in the invention include any nucleic acid vector molecule that can be engineered to encode and express one or more recombinant proteins in an appropriate (homologous) host cell. Such expression vectors include, without limitation, eukaryotic plasmid vectors, eukaryotic viral vectors, prokaryotic plasmids, bacteriophage vectors, shuttle vectors (e.g., a vector that can replicate in eukaryotic and prokaryotic cells), mini-chromosomes, and various artificial chromosomes. Preferably, an expression vector is a plasmid expression vector, more preferably, a plasmid expression vector that stably integrates into a eukaryotic host cell genome, and even more preferably, a plasmid expression vector that stably integrates into a host cell genome by non-homologous recombination.

In another embodiment, the invention provides a host cell that contains an expression vector comprising a rEVE described herein and a recombinant gene that directs the expression of at least one recombinant protein in the host cell. A host cell may be a eukaryotic or prokaryotic host cell. Preferred eukaryotic host cells for use in the invention include, without limitation, mammalian host cells, plant host cells, fungal host cells, eukaryotic algal host cells, protozoan host cells, insect host cells, and fish host cells. More preferably, a host cell useful in the invention is a mammalian host cell, including, but not limited to, a Chinese hamster ovary (CHO) cell, a COS cell, a Vero cell, an SP2/0 cell, an NS/0 myeloma cell, a human embryonic kidney (HEK 293) cell, a baby hamster kidney (BHK) cell, a HeLa cell, a human B cell, a CV-1/EBNA cell, an L cell, a 3T3 cell, a HEPG2 cell, a PerC6 cell, and an MDCK cell. Particularly preferred is a CHO cell that can be treated with a standard methotrexate treatment protocol to amplify the copy number of recombinant genes on an expression vector inserted into the host cell. Fungal cells that may serve as host cells in the invention include, without limitation, Ascomycete cells, such as *Aspergillus, Neurospora*, and yeast cells, particularly yeast of a genus selected from the group consisting of *Saccharomyces, Pichia, Hansenula, Schizosaccharomyces, Kluyveromyces, Yarrowia*, and *Candida*. Preferred yeast species that may serve as host cells for expression of recombinant proteins according to the invention include, but are not limited to, *Saccharomyces cerevisiae, Hansenula polymorpha, Kluyveromyces lactis, Pichia pastoris, Schizosaccharomyces pombe*, and *Yarrowia lipolytica*. Prokaryotic host cells that may be used for expressing recombinant proteins according to the invention include, without limitation, *Escherichia coli*, serovars of *Salmonella enterica, Shigella* species, *Wollinella succinogenes, Proteus vulgaris, Proteus mirabilis, Edwardsiella tarda, Citrobacter freundii, Pasteurella* species, *Haemophilus* species, *Pseudomonas* species, *Bacillus* species, *Staphyloccocus* species, and *Streptococcus* species. Other cells that may be used as host cells for expression of recombinant proteins according to the invention include protozoan cells, such as the trypanosomatid host *Leishmania tarentolae*, and cells of the nematode *Caenorhaditis elegans*.

REVE polynucleotides as described herein, vectors comprising one or more rEVEs described herein, and host cells comprising such vectors comprising one or more rEVEs as described herein may be used in a variety methods related to expression of recombinant proteins of interest.

In one embodiment, the invention provides a method of enhancing expression of a recombinant protein of interest in a host cell comprising the step of inserting into a host cell a recombinant expression vector that comprises a rEVE described herein and a recombinant gene that encodes and directs the synthesis of the recombinant protein of interest in the host cell and culturing the host cell under conditions promoting expression of the recombinant protein.

In another embodiment, the invention provides a method of producing methotrexate-resistant host cells that stably (as opposed to transiently) express a recombinant protein at an elevated level in the absence of methotrexate ("MTX"), i.e., in the absence of the selective pressure for elevated expression of the recombinant protein provided by the presence of methotrexate. Such a method comprises the step of inserting into host cells an expression vector that comprises a recombinant gene encoding a recombinant protein of interest, a rEVE described herein, and a gene encoding a dihydrofolate reductase ("DHFR"); growing the host cells in the presence of methotrexate to select for a methotrexate-resistant host cell that expresses the recombinant protein of interest; and isolating a methotrexate-resistant host cell, wherein the methotrexate resistant host cell expresses the recombinant protein of interest at a level that is higher than that of a methotrexate-sensitive host cell, and wherein the methotrexate-resistant host cell stably expresses an elevated level of the recombinant protein of interest when grown in the presence or in the absence of methotrexate. In a particularly preferred embodiment, the rEVE used in this method comprises the sequence of SEQ ID NO:2 or an expression enhancing portion thereof that, when present on the same expression vector as a gene encoding a recombinant protein of interest, enhances the level of expression of the recombinant protein in a host cell.

In another embodiment, the invention provides a method for producing a population of host cells with enhanced or improved adaptation to the presence of methotrexate in a DHFR-methotrexate procedure for amplifying recombinant protein expression comprising the step of inserting into host cells an expression vector comprising a gene encoding a recombinant protein of interest, a rEVE described herein, and a DHFR gene, wherein a population of the host cells containing the expression vector adapts better, i.e., has a higher survivability and/or higher growth rate, in the presence of methotrexate compared to a population of host cells carrying the expression vector lacking the rEVE sequence.

In yet another embodiment, the invention provides a method of enhancing the amplification (elevation) of expression of a recombinant protein in host cells obtained using a DHFR-methotrexate procedure comprising the step of inserting into host cells an expression vector comprising a recombinant gene encoding a recombinant protein of interest, a rEVE described herein, and a DHFR gene; growing the host cells in the presence of methotrexate to select for a methotrexate-resistant host cell that expresses the recombinant protein of interest; and isolating an methotrexate-resistant host cell, wherein the isolated methotrexate-resistant host cell expresses the recombinant protein of interest in the presence of methotrexate at a level that is higher than that of a methotrexate-resistant host cell containing the same expression vector lacking a rEVE.

Methotrexate may be conveniently employed in methods described herein in a range of 20 nM to 500 nM, although lower and higher concentrations, such as 5 nM to 10 µM, may also be successfully employed in such methods to select for amplified expression of recombinant proteins of interest.

In still another embodiment, the invention provides a method of lowering, substantially suppressing, or essentially silencing expression of a recombinant protein from an expression vector. Such methods employ expression vectors that comprise one or more fragments of a rEVE that provides lower levels of expression of a particular recombinant gene product than provided using a rEVE comprising the sequence of SEQ ID NO:1 or SEQ ID NO:2. Such fragments have a particular truncated variant of SEQ ID NO:2, including a nucleotide base sequence of bases 1-1086 of SEQ ID NO:2 or of bases 1-461 of SEQ ID NO:2. A nucleic acid molecule having the truncated ARM2 sequence consisting of bases 1-461 of SEQ ID NO:2 is particularly useful in suppressing or substantially silencing expression of a recombinant protein from a vector molecule in a host cell. These findings also indicate that the sequence of nucleotide bases 462-2422 of SEQ ID NO:2 and the sequence of nucleotide bases 1087-2422 of SEQ ID NO:2 are most preferred for maximal rEVE-mediated enhancement of expression of recombinant proteins.

A recombinant protein whose expression may be enhanced by one or more rEVE molecules described herein may be any protein (including peptides, polypeptides, and oligomeric proteins) for which a functional gene(s) can be engineered into a nucleic acid vector molecule for expression in an appropriate host cell. Such proteins include, without limitation, soluble proteins, membrane proteins, structural proteins (i.e., proteins that provide structure or support to cells, tissues, or organs), ribosomal proteins, enzymes, zymogens, antibody molecules, cell surface receptor proteins, transcription regulatory proteins, translation regulatory proteins, chromatin proteins (e.g., histones), hormones, cell cycle regulatory proteins, G proteins, neuroactive peptides, immunoregulatory proteins (e.g., interleukins, cytokines), blood component proteins, ion gate proteins, heat shock proteins, dihydrofolate reductase, an antibiotic resistance protein, functional fragments thereof, epitope-containing fragments thereof, and combinations thereof.

Nucleic acid molecules containing a sequence of a rEVE described herein or portion thereof may also be used in as nucleic acid probes for identifying the presence of rEVE sequences in other nucleic acid molecules by nucleic acid hybridization or as a source of primers for use in various polymerase chain reaction (PCR) procedures, e.g., as may be employed for manipulating, identifying, producing, or amplifying rEVE sequences described herein.

REVE sequences, such as those for ARM1 (SEQ ID NO:1) and for ARM2 (SEQ ID NO:2), may comprise one or more matrix attachment region (MAR) sequences. MAR sequences may occur in clusters within a rEVE sequence, including in clusters at the 5' and/or 3' terminal regions of a rEVE sequence. REVE polynucleotides as described herein are a useful source of MAR sequences. Accordingly, the invention provides compositions and methods that are useful for increasing MAR sequences in a nucleic acid molecule comprising inserting into the nucleic acid molecule a rEVE described herein or a portion of a rEVE described herein containing one or more MAR sequences.

Nucleotide base sequences described herein also serve to provide the complementary sequences thereof. DNA molecules and nucleotide base sequences described herein also provide the corresponding RNA molecules and base sequences, wherein thymine (T) is replaced by uracil (U), and nucleic acid sequences complementary thereto.

DETAILED DESCRIPTION OF THE INVENTION

Figure 1:
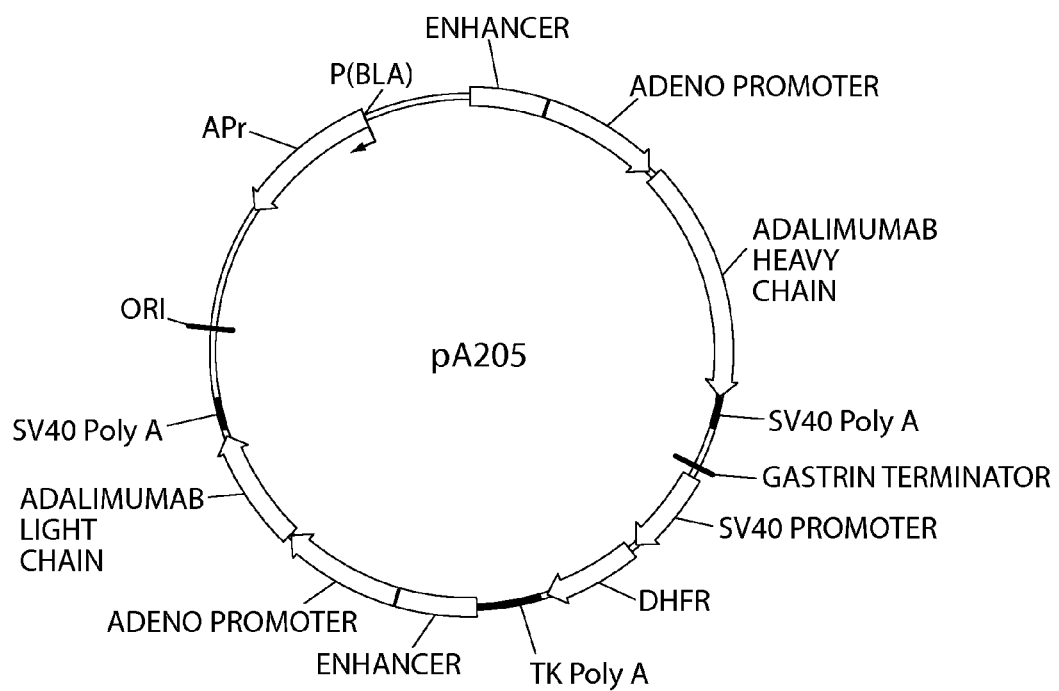
FIG. 1 shows a schematic diagram of plasmid expression vector pA205 used to express the immunoglobulin heavy and kappa light chains that form an active human anti-TNF-α IgG1 molecule ("adalimumab") in stable transfectants of Chinese hamster ovary (CHO) cells. Abbreviations: "ENHANCER" refers to the intermediate early gene enhancer of cytomegalovirus (CMV); "ADENO PROMOTER" refers to the major late promoter of adenovirus; "ADALIMUMAB HEAVY CHAIN" refers to the coding region for IgG1 heavy chain of adalimumab; "SV40 Poly A" refers to the simian virus 40 polyadenylation site; "GASTRIN TERMINATOR" refers to the transcription termination signal of the human gastrin gene; "SV40 PROMOTER" is the simian virus 40 promoter; "DHFR" refers to mouse dihydrofolate reductase gene; "TK Poly A" refers to the polyadenylation site of the herpes simplex virus thymidine kinase gene; "ADALIMUMAB LIGHT CHAIN" refers to the coding region for kappa light chain of adalimumab; "ORI" refers to the plasmid ColE1 prokaryotic origin of replication that functions in *Escherichia coli*; "P(BLA)" refers to the prokaryotic promoter of the β-lactamase gene (ampicillin resistance gene) and small arrow indicates direction of transcription; "APr" ("ampicllin resistance") refers to the coding region for β-lactamase. Arrows indicate direction of transcription (5' to 3').

This invention is based on the discovery that one or more isolated nucleic acid molecules (polynucleotide molecules) comprising a nucleotide sequence of SEQ ID NO:1:

aattgaattcgttcccctttagtgagggttaattccgcggccgcgtcg
acagctctagagggagtgccaggataggctccaaagctacacagaga
atccctgtttcaaaaaaccaaaaaaaaaaaaaataaaaaataaaaaat
aaaaagtagggtacagatctaaatagacaattctcaatagaggaatc
taaaatgcctgaaagacaaataagaaagtgttcaacatccttagcca
tcagggaaatgcaaatcaaaacaactctgagatactatcttactcct
gtcataatggccaaattcaaaaacactaatgacagttcatgttggag
agaatgtggagaaagaggagcacttctccactgctggtgggagtgcc
aacttggacagccactttggaaatcagtatggctactcctcaagaaa
atggaaatcagtttaccacaagatccagcaattccactcaggcatat
acccaaaagaaccgcattcatacaagcaatatctgttcaacgatgtt
catagcagctctatttgtaacagccagaaactggaagcagcctagtt
gcacctcaaccaaagaaatggatagagaaaatatggtacatttatgc
aatggagtactactcagcggaaaagtacaatggaatcttgaaatttg
caagaaaatggatggaactagaagaaacctttctgagcaaggtaact
caatcacaaaaagacaaacatgatatgtaatcactcatatgtggatt
ttagacacagtgtaaaggattaccagcctacaatccacactgccaaa
gaacctaataaacaaggaggaccctaagggagacatacatggtcccc
tggagatggggaatgggtcaagatatgctgagcaaagtgggaacatg
ggaagaggggggaaggagctaggaaattgagaaagggagaaaaggag
ggatgcagaggacataagggagcagaaacattgactcagggaatgaa
tcgaagataacaagccatgagatatcataatagagggagacattttt
gggtatacagagaaatcaggcacttgggaaatgtctggaaatctaca
aagtataacaccaggtaacaatctaagcaacagaggagaggctacct
taaatgtcctaccctgatagtgagattgatgactaacttatatgcca
tgttatagccttcatccagcagctggtggaagtagaagcagacaccc
ataactaatcacggaactgaactggaacccagattcagagaaggatg
agtgaagggcacagaggtccagaccaggctggtgaaacccacaaaaa
cagttgaactgaatatcggtgaactcttgctcccccagactgatagct
ggaataccagcatgggactgatccagactccaggaacatgagttcct
gtgaggaaacctcggaaatctaagggacctcctgtagaagttcagta -continued cttatccctagcataggtgtggactgagggagcccattccatataga
ggaatactctctggagccaacacacatgggggtgggcataggcccctt
tcccaaagcatacaatagactcggatgacaccctatggaaggcctca
tcatccagggggagcagaaaggatatgtgatagacagggtttcagtt
gggagccgggtagtgggagggggagaattggtggaagaaggaaaccgg
gattgtcatgtaaatcaatgctgtttctaattcaaataagaaagttg
aaaaaaaagaaaactgatacttattgcaccatgtaatgttatgaaat
ggcatttgctgttaagatgagcagtctatctgctaatctccctagct
ggcttgtgaacttgttatatggacaaagctggtctcaaattcaaaga
tatttgcgtatgtctgtctcctgagtgttgagagtacaagtatgtac
caccaatcccctttgattatacaattacatttgaaaacagtttgagat
ttaattataactatgcaatcaattcaaaataataaatttaaatctca
tatttgtctttaggtggaaatctgttaatatacatcatgattatata
ttttaatttattatatgttttctaggacaaaatatactaaaatgaaa
tctaaggctctaaacatacaaaactgtatgcatagatacatcacgat
catataatttccatgacatgctattcgggaatataatgatctacctg
cagtaatgattaatttggaaatgctgaatacaactgcttctcttttg
aaaatacaaattccttacatttgtaatctatttaattttaaaggttg
taccccagaaagtagtgaattcttaa, or a nucleotide sequence of SEQ ID NO:2:

aagaatatgctcaatgtaatacccatggcaggcattcaatgtttgtc
tgtcttcatattgaagataaacagatgtatatcatatacaaaaatat
ttaatgtgaagttgtccatgtgttcaggatctatatactttcaaaaa
tcttttttccatattcttttcttaatcctcctgaagtgtagaccatta
tactggaaaaccgtcactattgtacaggataggagcctttgactctg
agaggatcccatacattgattgtattttcaaatatattttggctgct
tttctccatgtgatatttggcaatctggagaggcatttgctcctgga
aatttatcaatgttgacaatgttgtttacatgttttaagtaactatt
ttgctaccaaggaaactgcttcactccctttcacatataaaactcat
aaaatattgaaaggctccaataagtttaaatcattctgtattgctca
tggagatttaaatttcagtgctaattttttattagcactttaattta
gaaggcaccaggtttctacaagatttaaaattattggagcatttcaa
aattttataagctttccagtaaggttgtggctatgattctttgcttg
taaagtaaagtgcaatttaaagttaatttaaataatttaactgctgc
agacattttaggagaattgtttgtatttcaaactgaaattcagggta
gacaattagaataattttacaaagaggaaatattttttctaataataa
attagtaactctaacttatattaaaatttaagtcctcattgctttca
atatttaacaaccctattgtattattttcttataaatatttgaat
ttataatgatcaaagaatttctttgatacaagtgtctaaatgattac -continued
```
catcaaactgttggtaggagcttgttatatatgtgttttaccttatg tttttgatacttcatttgttactgtactgtgatcgagttaattccc tactgaaactaaaaatgctatcacatagttttagcatcatctgttgg ggaaatggctattttaactactctgagatgagaaattcaacaccatt cactaacaatatagggaaactagtgttggtagattgttgagtgctta tacatatatcttgtcccatggttaactataagttggtgtctgttgct gccacccagtatggaaacacattatgttttttcttttttttttttta tagccatgagaaagaccaaaattctatacttgaaaaaccgtttatat tgaatgtgtattcctttcacgtccaccttagattcaactcctaagtc aatttatggtaaagcatagatcatctgcttgacaacagtttggatga tgatcttggaaaaaatgccttattatatgatacaatggaattaatga tatgagctgaataaatatcaatattcaaatgacatactaatatttt atgtctaagagaatgtgttcaaagtagatgaaagtgccttcacttga aaattcatctgagttaaaacagatagttgcttcggttttagttattt cagaggtattcaagttgacaactaagaatagccgtcacagatacata tcaattatggacccaaattctattgaatgtcagctacatattcttat agaaataggaacctagatgaggccgtgttcttggaatgaattttca acacattgtatgagggttttattgtggttttggttgttgttttactt tccttttttttccatagacaaatttgtcccatgtacccacaaggtgac cagtggtgacaagcctactccaggagtcctggtgaataaagattata caagatagtagagactcatcaaaacaataagaaaaagagaatacata gggcagaaatttctcatttctcagctatggtatcctatttcactct tgtactattctactcactagaagtcagtgactaccataactcagtgg ctgtgccctagatcaaaggaaacattatttcaaggcatgaatgtcag ccacaccttcatagtgggttacttttaatttgtttagtaagaataga caccctactttggttaggaaacataaacttacaagacattcattggt ttttctttactaaattaaatcattaagaaaacgtaattatcagagtt taaatggcatgaaacatagaaatactcatttgctgccctgatttatt ttcccaagaatattttcaatgtcttctttggaagctccttggtaaat gcactttctttcactcatttatgaggtctgtgcacatcacagtcaat aaaggcctgcagtattgaatcagccatacagacataattcataacat ttttctatttctcatgaatcaaatattgttattgctgtacataaaat aatgaatcaaagtataggtctaga,
``` can be engineered into expression vector molecules to enhance expression of one or more recombinant proteins from one or more genes present on the expression vector molecules.

An isolated polynucleotide molecule that comprises a nucleotide sequence of SEQ ID NO:1 or SEQ ID NO:2 is referred to herein as a recombinant expression vector element (rEVE). REVEs of the invention also include, but are not limited to, a polynucleotide molecule that comprises an expression-enhancing portion of the sequence shown in SEQ ID NO:1 ("ARM1") or SEQ ID NO:2 ("ARM2"). Sequences from the 3' terminal region of the ARM2 SEQ ID NO:2, such as those having the sequence of bases 462-2422 of SEQ ID NO:2 and of bases 1087-2422 of SEQ ID NO:2, are particularly useful in providing enhanced expression of a recombinant protein of interest. A rEVE described herein may be used in combination with other control sequences, regulators, and procedures currently available to increase production of recombinant proteins in host cells.

In order to more clearly describe the invention the following terms are defined:

The term "antibody" or "antibody molecule", as used and understood herein, broadly refer to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibodies are known in the art and include the non-limiting embodiments discussed below.

In a full-length antibody, each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain (CL). The VH and VL regions can be further subdivided into regions of hypervariability, termed complementarity determining regions (CDR), interspersed with regions that are more conserved, referred to as framework regions (FR). Each VH and VL is composed of three CDRs and four FRs, arranged from amino terminus to carboxy terminus in the following order: FR1, CDR1, FR2, CDR2, FR3, CDR3, FR4. Immunoglobulin molecules can be of any type (e.g., IgG, IgE, IgM, IgD, IgA, and IgY), class (e.g., IgG1, IgG2, IgG 3, IgG4, IgA1 and IgA2), or subclass.

The terms "antibody" and "antibody molecule" also encompass one or more fragments of an antibody that retains the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antibody" include a Fab fragment, i.e., a monovalent (one binding site) fragment consisting of the VL, VH, CL, and CH1 domains; a F(ab')$_2$ fragment, i.e., a bivalent (two binding sites) fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) (Ward et al., Nature, 341: 544-546 (1989); Winter et al., PCT publication WO 90/05144 A1, incorporated herein by reference), which comprises a single variable domain; dual variable domain (DVD) antibodies (see, e.g., PCT Publication No. WO 2007/024715); and isolated complementarity determining regions (CDRs). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv), see e.g., Bird et al. Science, 242: 423-426 (1988); Huston et al., Proc. Natl. Acad. Sci. USA, 85: 5879-5883 (1988)). Such single chain antibodies are encompassed by the terms "antibody" and "antibody molecule". Diabodies are also encompassed by the terms "antibody" and "antibody molecule". Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., *Proc. Natl. Acad. Sci. USA*, 90: 6444-6448 (1993); Poljak, R. J., *Structure*, 2: 1121-1123 (1994)). The terms "antibody" and "antibody molecule" also encompass dual variable domain immunoglobulin molecules, such as DVD-IG™ (Abbott Laboratories) dual variable domain immunoglobulin molecules (see, e.g., PCT publication No. WO 2007/024715).

As used herein, "vector" refers to any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate (homologous) host cell.

Expression vectors may include, without limitation, eukaryotic plasmid vectors, eukaryotic viral vectors, prokaryotic plasmids, bacteriophage vectors, shuttle vectors (e.g., a vector that can replicate in eukaryotic and prokaryotic cells), mini-chromosomes, and various artificial chromosomes (e.g., bacterial artificial chromosomes (BACs), yeast artificial chromosomes (YACs)). Preferably, an expression vector used in the invention is a plasmid, more preferably, a plasmid expression vector that stably integrates into a host cell genome, and, even more preferably, a plasmid expression vector that stably integrates into a host cell genome by non-homologous recombination. A "shuttle vector" (or bi-functional vector) refers to any vector that can replicate in more than one species of organism. For example, a shuttle vector that can replicate in both *Escherichia coli* (*E. coli*) and *Saccharomyces cerevisiae* (*S. cerevisiae*) can be constructed by linking sequences from an *E. coli* plasmid with sequences from the yeast 2μ plasmid.

Expression systems comprise an expression vector and appropriate (homologous) host cell that will express the recombinant protein(s) encoded on the expression vector. An expression system may be a stable expression system or a transient expression system. In a stable expression system, an expression vector stably integrates into the host cell genome or is continuously replicated and faithfully passed on to both daughter cells so that host cells are able to continue to express the recombinant protein(s) when cultured under the appropriate conditions. In a transient expression system, expression vector molecules are not retained in both daughter cells and eventually are lost or so diminished in a growing cell culture that expression of recombinant protein(s) from the culture will eventually cease or be so low as to not be useful for most production purposes. Expression vectors used in the Examples, below, are types of shuttle vectors that can replicate to relatively high copy numbers when inserted (e.g., by transformation) into *E. coli* cells and that can also be inserted (e.g., by transfection) into and stably maintained in Chinese hamster ovary (CHO) cells to obtain stable expression of their encoded gene product(s) of interest (Kaufman et al., *Molec. Cell. Biol.*, 5: 1750-1759 (1980)) or that can be transiently maintained in HEK 293 cells (Durocher et al., *Nucleic Acids Res.*, 30: E9). Thus, a rEVE polynucleotide molecule described herein may be used to enhance expression of a recombinant protein(s) of interest in both stable and transient expression systems.

Exemplary eukaryotic vectors that may be used in the invention include, but are not limited, to viral and non-viral vectors. Viral vectors include, without limitation, retroviral vectors (including lentiviral vectors); adenoviral vectors including replication competent, replication deficient, and gutless forms thereof; adeno-associated virus (AAV) vectors; simian virus 40 (SV-40) vectors; bovine papilloma virus vectors; Epstein-Barr virus vectors; herpes virus vectors, vaccinia virus vectors; Moloney murine leukemia virus vectors; Harvey murine sarcoma virus vectors, murine mammary tumor virus vectors, and Rous sarcoma virus vectors. Baculovirus vectors are well known and are suitable for expression in insect cells.

A variety of vectors suitable for expression in eukaryotic or prokaryotic cells are well known in the art, and many are commercially available. Commercial sources include, without limitation, Stratagene (La Jolla, Calif.), Invitrogen (Carlsbad, Calif.), Promega (Madison, Wis.), and Sigma-Aldrich (St. Louis, Mo.). Many vector sequences are available through GenBank, and additional information concerning vectors is available on the internet via the Riken BioSource Center.

A vector molecule typically comprises at least one origin of replication and may also comprise a gene for a "marker" or "selectable marker" by which the vector can be identified or selected when inserted into a host cell. Such useful markers may, without limitation, confer resistance to antibiotics, provide functions that give a selective growth advantage over cells that lack such functions, or provide a means to easily identify cells that possess the vector (e.g., colorigenic system). Such markers are well known in the art, and the choice of the proper selectable marker(s) to use in a vector molecule will depend on what host cell will be used and what properties are desired of the host cell containing the vector.

The terms "functional gene construct", "functional gene", and "gene" refer to a polynucleotide that contains a coding sequence for one or more proteins that is operably linked to a promoter sequence and possibly other transcriptional regulatory sequences to direct proper transcription of the coding sequence into messenger RNA (mRNA) and that also comprises any of a variety of translation regulatory sequences that may be necessary or desired to direct proper translation of the mRNA into the desired protein in the intended host cell. A translational start codon (e.g., ATG) and a ribosome binding site are typically required in the mRNA for translation to occur in prokaryotic and eukaryotic cells. Other translation regulatory sequences that may also be employed, depending on the host cell, include, but are not limited to, an RNA splice site and a polyadenylation site.

The term "recombinant" is used herein to describe altered or manipulated nucleic acids, nucleic acids isolated from the environment in which they naturally occur, host cells transfected with or otherwise manipulated to contain exogenous nucleic acids, or proteins expressed non-naturally through manipulation of isolated DNA and transformation of host cells. "Recombinant" is a term that specifically encompasses DNA molecules which have been constructed in vitro using genetic engineering techniques, and use of the term "recombinant" as an adjective to describe a molecule, construct, vector, cell, protein, polypeptide, or polynucleotide specifically excludes naturally occurring such molecules, constructs, vectors, cells, proteins, polypeptides, or polynucleotides. In particular, a "recombinant protein" for the purposes of the present invention is a protein that is expressed by a host cell which has been manipulated by incorporating at least one genetic element that was not naturally occurring in the host cell prior to expression of the protein. A protein, the coding sequence for which has been artificially incorporated into a host cell made capable of expressing the protein, for example by being transfected with an expression vector including the coding sequence of the protein, is a "recombinant protein" once expressed by the host cell.

A "host cell" refers to any cell, i.e., any eukaryotic or prokaryotic cell, into which a vector molecule can be inserted. According to the present invention, preferred host cells are eukaryotic or prokaryotic cells, including, but not limited to, animal cells (e.g., mammalian, bird, and fish host cells), plant cells (including eukaryotic algal cells), fungal cells, bacterial cells, and protozoan cells. Host cells useful in the invention may be of any genetic construct, but are preferably haploid or diploid cells. Preferred mammalian host cells useful in the invention include, without limitation, a Chinese hamster ovary (CHO) cell, a COS cell, a Vero cell, an SP2/0 cell, an NS/0 myeloma cell, a human embryonic kidney (HEK 293) cell, a baby hamster kidney (BHK) cell, a HeLa cell, a human B cell, a CV-1/EBNA cell, an L cell, a 3T3 cell, an HEPG2 cell, a PerC6 cell, and an MDCK cell. A preferred insect cell is Sf9. Fungal cells that may serve as host cells in the invention include, without limitation, Ascomycete cells, such as *Aspergillus, Neurospora*, and yeast cells, particularly yeast of the genera *Saccharomyces, Pichia, Hansenula, Schizosaccharomyces, Kluyveromyces, Yarrowia*, and *Candida*. Particularly preferred yeast fungal species that may serve as host cells for expression of recombinant proteins are *Saccharomyces cerevisiae, Hansenula polymorpha, Kluyveromyces lactis, Pichia pastoris, Schizosaccharomyces pombe*, and *Yarrowia lipolytica*. Preferred prokaryotic cells that may serve as host cells in the invention include, without limitation, *Escherichia coli*, serovars of *Salmonella enterica, Shigella* species, *Wollinella succinogenes, Proteus vulgaris, Proteus mirabilis, Edwardsiella tarda, Citrobacter freundii, Pasteurella* species, *Haemophilus* species, *Pseudomonas* species, *Bacillus* species, *Staphyloccocus* species, and *Streptococcus* species. Other cells that may be useful host cells for the expression of recombinant proteins according to the invention include protozoans, such as the trypanosomatid host *Leishmania tarentolae*, and cells of the nematode *Caenorhaditis elegans*. Various expression vectors are available for use in the aforementioned cells.

There are a variety of means and protocols for inserting vector molecules into cells including, but not limited to, transformation, transfection, cell or protoplast fusion, use of a chemical treatment (e.g., polyethylene glycol treatment of protoplasts, calcium treatment, transfecting agents such as LIPOFECTIN® and LIPOFECTAMINE® transfection reagents available from Invitrogen (Carlsbad, Calif.), use of various types of liposomes, use of a mechanical device (e.g., nucleic acid coated microbeads), use of electrical charge (e.g., electroporation), and combinations thereof. It is within the skill of a practitioner in the art to determine the particular protocol and/or means to use to insert a particular vector molecule described herein into a desired host cell.

Methods for "transferring nucleic acid sequence information" from one vector or other nucleic acid molecule to another are not limiting in the present invention and include any of a variety of genetic engineering or recombinant nucleic acid techniques known in the art. Particularly preferred transfer techniques include, but are not limited to, restriction digestion and ligation techniques, polymerase chain reaction (PCR) protocols (utilizing specific or random sequence primers), homologous recombination techniques (utilizing polynucleotide regions of homology), and non-homologous recombination (e.g., random insertion) techniques. Nucleic acid molecules containing a specific sequence may also be synthesized, e.g., using an automated nucleic acid synthesizer, and the resulting nucleic acid product then incorporated into another nucleic acid molecule by any of the aforementioned methodologies.

Employing genetic engineering technology necessarily requires growing recombinant host cells (e.g., transfectants, transformants) under a variety of specified conditions as determined by the requirements of the cells and the particular cellular state desired by the practitioner. For example, a host cell may possess (as determined by its genetic disposition) certain nutritional requirements, or a particular resistance or sensitivity to physical (e.g., temperature) and/or chemical (e.g., antibiotic) conditions. In addition, specific culture conditions may be necessary to regulate the expression of a desired gene (e.g., the use of inducible promoters), or to initiate a particular cell state (e.g., yeast cell mating or sporulation). These varied conditions and the requirements to satisfy such conditions are understood and appreciated by practitioners in the art.

In the context of amplifying (elevating) recombinant protein expression in a host cell using a standard dihydrofolate reductase (DHFR)-methotrexate (MTX) amplification procedure, the terms "stability" and "stable expression" refer to the ability of a culture of cells to continue to express the recombinant protein at an amplified (elevated) level when grown in the absence of methotrexate, i.e., in the absence of the selective pressure for elevated expression provided by the presence of methotrexate used in the amplification procedure. Thus, once isolated, a stably transfectant host cell can express a recombinant protein of interest in the presence or absence of methotrexate.

In the context of amplifying recombinant protein expression in a host cell using a standard dihydrofolate reductase (DHFR)-methotrexate (MTX) amplification procedure, "enhanced adaptation" or "improved adaptation" to the presence of methotrexate refers to the higher survivability and/or higher growth rate in the presence of methotrexate of a culture of host cells carrying expression vectors comprising a rEVE described herein compared to the survivability and/or growth rate in the presence of methotrexate of a culture of host cells carrying expression vectors that lacks the rEVE. "Survivability" of a population of host cells refers to the ability of a population of host cells to grow and to reproduce in the presence of a selective pressure (e.g., methotrexate).

"Sequence homology" is a familiar concept to practitioners in this field. To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second comparison amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The nucleic acid sequence homology may be determined as the degree of identity between two sequences. The homology may be determined using computer programs known in the art, such as GAP software provided in the GCG program package. See, Needleman and Wunsch, *J. Mol. Biol.*, 48: 443-453 (1970).

A composition or method described herein as "comprising" one or more named elements or steps is open-ended meaning that the named elements or steps are essential, but other elements or steps may be added within the scope of the composition or method. To avoid prolixity, it is also understood that any composition or method described as "comprising" (or "comprises") one or more named elements or steps also describes the corresponding, more limited, composition or method "consisting essentially of" (or "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other unnamed element or step. In any composition or method disclosed herein, known or disclosed equivalents of any named essential element or step may be substituted for that element or step.

It is also understood that an element or step "selected from the group consisting of" refers to one or more of the elements or steps in the list that follows, including combinations of any two or more of the listed elements or steps.

Unless indicated otherwise, the meaning of other terms will be clear from the context or will be understood to be the same as understood and used by persons skilled in the art.

Persons skilled in the art also understand that a nucleic acid sequence (nucleotide base sequence) as described herein provides the DNA, RNA, and complementary sequences thereof.

Recombinant expression vector elements (rEVEs) of the invention were first isolated from the regions of genomic DNA flanking either side of the site of integration of an expression vector present in cells of a transfected DUXB11 CHO cell line that expressed exceptionally high levels of anti-IL-12 antibody molecules from genes present on the expression vector. Cloning and sequencing of these flanking regions of DUXB11 CHO genomic DNA revealed the sequence of SEQ ID NO:1 and of SEQ ID NO:2. The 2329 base sequence of SEQ ID NO:1 is also referred herein as "ARM1", and the 2422 base sequence of SEQ ID NO:2 is referred to as "ARM2". The flanking ARM1 DNA sequence was shown to be located upstream of the direction of transcription of the heavy chain gene of the integrated expression vector, and the flanking ARM2 DNA sequence was shown to be located downstream of the direction of transcription of the light chain gene of the integrated expression vector (see, Examples section, below).

ARM1- and ARM2-containing DNA molecules were inserted alone and in combination in expression vectors to determine whether their presence could affect the level of expression of various recombinant proteins in host cells containing the expression vectors. Both ARM1- and ARM2-containing DNA provide enhanced levels of expression of recombinant proteins in host cells compared to the levels of production obtained in the absence of these sequence (see, Examples, below). Accordingly, ARM1- and ARM2-containing nucleic acid molecules are examples of recombinant expression vector elements (rEVEs). Typically, the enhanced level of production obtained with an ARM1 polynucleotide is somewhat lower than that obtained with ARM2 polynucleotide or with a combination of ARM1 and ARM2 polynucleotides.

In all instances where either or both of ARM1 and ARM2 have been employed in the construction of expression vectors for the production of a recombinant protein of interest according to the invention, the level of expression of the protein was greater using the ARM1 and/or ARM2 expression enhancer elements. Increased comparative expression levels for the recombinant protein product of greater than 2-fold, greater than 3-fold, greater than 4-fold, greater than 5-fold, greater than 6-fold, greater than 9-fold, greater than 10-fold, greater than 13-fold, greater than 16-fold, and greater than 18-fold over control expression systems having no ARM enhancers were directly observed. (See Examples, below.) Moreover, the high level of expression obtained using expression vectors bearing ARM1 or ARM2, or both ARM1 and ARM2, is stably maintained over time in the transfected host cells.

ARM1 and ARM2 sequences possess regions that are relatively rich in sequences for matrix/scaffold attachment regions (MARS/SARs; see, e.g., Michalowski et al., *Biochemistry*, 38: 12795-12804 (1999); Tikhonov et al., *The Plant Cell*, 12: 2490-264 (2000) U.S. Pat. No. 7,129,062; Bode et al., *Int. Rev. Cytol.*, 162A: 389-454 (1995); Bode et al., *Crit. Rev. Eukaryotic Gene Expression*, 6: 115-138 (1996)). In the case of ARM1, MAR sequence motifs are particularly concentrated in the 3' terminal region of the sequence, whereas in the case of ARM2, clusters of MAR motifs appear in both the 5' and 3' terminal regions of the sequence with fewer MAR motifs situated in the middle region of the sequence. Deletion analysis indicates that an approximately 1260 base pair 3' terminal region of ARM2 nucleic acid contains sequences that are critical for ARM2 enhanced protein expression activity (see, Example 6, below).

The rEVE molecules of the invention include those nucleic acid molecules that comprise expression enhancing portions or fragments of the ARM1 and ARM2 sequences. Such expression enhancing portions of the ARM1 and ARM2 sequences are those that, when present on the same expression vector as a gene encoding a recombinant protein of interest, enhance the level of expression of the recombinant protein in a host cell containing the expression vector as compared to that level of expression obtained in the absence of such portions or fragments of ARM1 or ARM2 sequences.

A rEVE described herein may be used alone or in combination with any other regulatory element or expression enhancing system for elevating the level of production of a desired recombinant protein(s) in a host cell. Such other sequences and systems may include, without limitation, the use of regulated promoters to control or optimize transcription of the gene(s) encoding a recombinant protein(s) of interest, the use a signal sequence that directs secretion of recombinant protein(s) from the host cell, and the use of gene amplification methods, such as a dihydrofolate reductase (DHFR)-methotrexate (MTX) amplification protocol or a glutamine synthetase protocol. In a DHFR-MTX amplification procedure, host cells carrying an expression vector that comprises a gene for DHFR are selected for resistance to increasing concentrations of methotrexate (see, e.g., Kaufman, R. J., In *Genetic Engineering: Principles and methods* (ed. J. K. Setlow), volume 9, page 155 (Plenum Publishing, New York, 1987)). Typically, as the level of resistance to methotrexate increases, there is an accompanying amplification of the copy number of the recombinant gene(s) along with a corresponding amplification (elevation) in the level of recombinant protein expression from such amplified gene(s).

The nucleic acid sequences of SEQ ID NO:1 and SEQ ID NO:2 were identified from DNA molecules obtained from a DUXB11 CHO cell line. Any of a variety of methods may be used to produce nucleic acid molecules comprising a nucleotide sequence of SEQ ID NO:1, SEQ ID NO:2, or portions of either of these sequences. Such methods include, without limitation, cloning one or more rEVE DNA molecules comprising such sequences out of the genomic DNA of DUXB11 CHO cells, solid-phase nucleic acid synthesis protocols to produce a polynucleotide comprising such sequences, recombinant nucleic acid techniques, polymerase chain reaction (PCR) protocols, automated nucleic acid synthesizers, and combinations thereof. A rEVE polynulecotide molecule described herein may also be purchased from commercial suppliers of custom designed nucleic acid molecules. The method by which a rEVE is produced or synthesized is not limiting, and the skilled practitioner can decide which method or combination of methods is most appropriate for producing a particular rEVE described herein.

A rEVE described herein may be inserted into an expression vector to enhance expression of any of a variety of proteins (including peptides, polypeptides, and oligomeric proteins) from an expression vector in a host cell. Provided a nucleotide coding sequence(s) is known or available on a nucleic acid (DNA or RNA) molecule, the coding sequence(s) or the entire functional gene for a protein of interest may be inserted into an expression vector using any of a variety of methods available in the art. Coding sequences are operably linked to a promoter that will function in the type of host cell for which expression is desired. Additional transcriptional and translational sequences may also be engineered into the vector for the proper expression of the desired protein(s) in the host cell.

The expression of any of a vast variety of proteins (including peptides, polypeptides, oligomeric proteins) from an expression vector in an appropriate host cell may be enhanced by one or more rEVEs described herein, including, but not limited to, soluble proteins, membrane proteins, structural proteins (i.e., proteins that provide structure or support to cells, tissues, or organs), ribosomal proteins, enzymes, zymogens, various antibody molecules (including, but not limited to, antibodies to TNF-α, such as adalimumab; antibodies to selectins; antibodies to immunoregulatory proteins, such as antibodies to IL-13; dual variable domain immunoglobulin molecules, such as DVD-IG™ dual variable domain immunoglobulin molecules; antibodies to cell surface receptors), cell surface receptor proteins, transcription regulatory proteins, translation regulatory proteins, chromatin proteins, hormones, cell cycle regulatory proteins, G proteins, neuroactive peptides, immunoregulatory proteins (e.g., interleukins, cytokines, lymphokines), blood component proteins, ion gate proteins, heat shock proteins, dihydrofolate reductase, an antibiotic resistance protein, a functional fragment of any of the preceding proteins, an epitope-containing fragment of any of the preceding proteins, and combinations thereof.

A recombinant protein of interest may be produced by transcribing and translating the gene or genes that encode the recombinant protein and are present on an expression vector molecule described herein. Such transcription and translation of the gene or genes on an expression vector, including those described herein, may be carried out using a cell-free transcription/translation system or using an appropriate host cell that contains the expression vector molecule and that has the proper cellular transcription and translation machinery necessary to produce the recombinant protein of interest from the gene or genes present on the expression vector molecule.

Matrix attachment regions (MARs), also referred to as scaffold attachment regions (SARs), were originally identified as fragments of chromosomal DNA that bind to preparations of nuclear proteins that appear to form a scaffold or matrix in the eukaryotic nucleus. MARs are believed to reside in loops of chromatin that attach to the nuclear matrix and to define or delimit individual structural units of chromatin. MARs have been associated with some enhancer sequences and/or linked to a number of processes that may occur in chromatin, including transcription, transgene expression, transgene rearrangement, recombination, replication, and stabilization of transfections (see, e.g., Michalowski et al., *Biochemistry,* 38: 12795-12804 (1999); Zhong et al., *Proc. Natl. Acad. Sci. USA,* 96(21): 11970-11975 (1999); Tikhonov et al., *The Plant Cell,* 12: 249-264 (2000); Zhou et al., *Gene,* 277: 139-144 (2001); Sumer et al., *Genome Research,* 13: 1737-1743 (2003); U.S. Pat. No. 7,129,062; Bode et al., *Int. Rev. Cytol.,* 162A: 389-454 (1995); Bode et al., *Crit. Rev. Eukaryotic Gene Expression,* 6: 115-138 (1996)). ARM1 (SEQ ID NO:1) and ARM2 (SEQ ID NO:2) possess a variety of MAR elements, which appear to be located predominantly in clusters in the 3' and/or 5' terminal regions. ARM1 contains a cluster of MAR elements in the 3' terminal region. In the case of ARM2, MAR elements can be found throughout the length of this rEVE sequence with clusters of MAR motifs located in both the 5' and the 3' terminal regions. Clearly, vectors and other nucleic acid molecules carrying ARM1 and ARM2 sequences are convenient sources of MAR elements and clusters of MAR elements. Accordingly, ARM1, ARM2, and MAR-containing portions thereof may be used to increase the number of MAR elements in a nucleic acid molecule of interest using any of the various methods available in the art for recombining or otherwise transferring nucleic acid sequence information to a nucleic acid molecule.

Nucleic acid molecules comprising a sequence of a rEVE described herein or a portion thereof may also be used in a variety of procedures known in the art to manipulate, identify, produce, or amplify rEVE sequences in other nucleic acid molecules. Such procedures may include, without limitation, use of a rEVE or portion thereof as a probe in any of the various nucleic acid hybridization methods known in the art or as a primer in any of the various polymerase chain reaction (PCR) procedures known in the art.

A rEVE polynucleotide molecule described herein may be used in methods to produce a recombinant protein of interest. Preferably, such a method of producing a recombinant protein of interest comprises a recombinant expression vector as described herein that comprises one or more recombinant genes encoding the recombinant protein of interest and at least one rEVE polynucleotide molecule described herein, and transcribing and translating the one or more recombinant genes present on the recombinant expression vector to produce the recombinant proteins of interest. The transcription and translation of the one or more recombinant genes from the expression vector is preferably carried out in a host cell that comprises the expression vector and is cultured under conditions promoting expression of the recombinant protein of interest. A rEVE polynucleotide molecule may be used to enhance the level of expression of one or more recombinant proteins of interest from an expression vector in a host cell, whether transiently expressed (e.g., in a transfected COS or HEK 293 host cell) or stably expressed (e.g., in a transfected CHO host cell). Transcription and translation of one or more recombinant genes from an expression vector that carries a rEVE as described herein may also be carried out using an in vitro cell-free transcription/translation system available in the art.

A rEVE polynucleotide molecule described herein may be used in preparing a host cell that stably (as opposed to transiently) expresses elevated levels of a recombinant protein when the level of expression has been amplified (elevated)

using a DHFR-methotrexate amplification procedure. Such host cells are methotrexate-resistant (MTX-resistant) cells that will continue to express elevated levels of a recombinant protein not only when grown in the presence of methotrexate, but also when grown in the absence of methotrexate, i.e., when grown in the absence of the selective pressure for elevated expression provided by the presence of methotrexate. In a preferred embodiment, such a method to produce a methotrexate-resistant host cell comprises the steps of:
  inserting into host cells an expression vector comprising:
    a recombinant gene coding for a recombinant protein of interest,
    a rEVE or expression enhancing portion thereof, and
    a dihydrofolate reductase (DHFR) gene,
  growing the host cells in the presence of methotrexate to select for a methotrexate-resistant host cell that expresses the recombinant protein of interest, and
  isolating a methotrexate-resistant host cell;
wherein the isolated methotrexate-resistant host cell expresses the recombinant protein of interest at a level that is higher than that of a methotrexate-sensitive host cell, and wherein said methotrexate-resistant host cell stably expresses an elevated level of the recombinant protein when grown in the presence or in the absence of methotrexate. Preferably, the rEVE comprises SEQ ID NO:1, SEQ ID NO:2, or an expression enhancing portion thereof. More preferably, the rEVE comprises SEQ ID NO:2.

The rEVE polynucleotide molecules described herein may also be used in a method of improving the ability of a population of host cells that express a recombinant protein to adapt to growth in the presence of methotrexate. In a preferred embodiment, such a method comprises:
  inserting into host cells an expression vector comprising:
    a recombinant gene encoding a protein of interest,
    a recombinant expression vector element (rEVE) polynucleotide molecule comprising a sequence selected from the group consisting of SEQ ID NO:1, SEQ ID NO:2, a portion SEQ ID NO:1, a portion of SEQ ID NO:2, and combinations thereof, and
    a dihydrofolate reductase (DHFR) gene;
wherein a population of the host cells containing the expression vector has a higher survivability and/or higher growth rate when grown in the presence of methotrexate compared to a population of host cells carrying the expression vector lacking said rEVE polynucleotide molecule.

A rEVE polynucleotide molecule described herein may also be employed to enhance the amplification (elevation) of expression of a recombinant protein in host cells using a DHFR-methotrexate amplification procedure. In a preferred embodiment, such a method comprises:
  inserting into host cells an expression vector comprising:
    a recombinant gene coding for a recombinant protein of interest,
    a rEVE polynucleotide molecule comprising a sequence selected from the group consisting of SEQ ID NO:1, SEQ ID NO:2, a portion of SEQ ID NO:1, a portion of SEQ ID NO:2, and combinations thereof, and
    a dihydrofolate reductase (DHFR) gene,
  growing the host cells in the presence of methotrexate to select for a methotrexate-resistant host cell that expresses the recombinant protein of interest, and
  isolating the methotrexate-resistant host cell,
wherein the isolated methotrexate-resistant host cell expresses the recombinant protein of interest in the presence of methotrexate at a level that is higher than that of a methotrexate-resistant host cell containing an expression vector lacking said rEVE polynucleotide molecule.

In methods described herein that employ a methotrexate selection for amplified expression of a desired recombinant protein(s), methotrexate may be used in the range of 20 nM to 500 nM. However, advantageously persons skilled in the art recognize that lower and higher methotrexate concentrations, such as 5 nM to 10 µM, may also be successfully employed in methotrexate selections to amplify expression (see, e.g., Kaufman, R. J., *Methods in Enzymology*, Vol. 185: 537-566 (1990)).

The invention also provides a method of lowering, substantially suppressing, or essentially silencing expression of a recombinant protein from an expression vector. Such a method may employ an expression vector that comprises one or more fragments of a rEVE sequence described herein that provide lower levels of expression of a particular recombinant gene product than provided using a full-length rEVE sequence. Such expression-lowering or expression-suppressing rEVE-derived sequences include a truncated variant of the sequence of ARM2 having the base sequence of bases 1-1086 of SEQ ID NO:2 or bases 1-461 of SEQ ID NO:2. Clearly, the presence of the 3' terminal sequence region deleted from these two variants is highly desirable for rEVE-mediated enhanced expression of recombinant proteins. A nucleic acid molecule having the ARM2 truncated sequence of bases 1-461 of SEQ ID NO:2 is particularly useful in suppressing or substantially silencing expression of a recombinant protein from an expression vector molecule in a host cell. Such methods may find use in a number of situations, including, without limitation, when there is a concern that expression of a recombinant protein may be toxic to the host cells or when some level of expression may present problems to purification or isolation of the desired protein, such as protein aggregation.

Thus, the sequence of bases 462-2422 of SEQ ID NO:2 and the sequence of bases 1087-2422 of SEQ ID NO:2 are most preferred for maximal ARM2 rEVE-mediated enhancement of expression of recombinant proteins. Accordingly, rEVE polynucleotides that are particularly useful for enhancing expression of recombinant proteins comprise the sequence of bases 462-2422 of SEQ ID NO:2 and/or the sequence of bases 1087-2422 of SEQ ID NO:2.

Additional embodiments and features of the invention will be apparent from the following non-limiting examples.

EXAMPLES

Example 1

Cloning and Sequence Analysis of ARM1 and ARM2 Recombinant Expression Vector Elements (rEVEs)

A production DUX B11 CHO cell line carrying a stably integrated expression vector was studied to determine the possible basis for the exceptionally high level of expression of a recombinant anti-IL-12 antibody encoded on the expression vector with which the host CHO cells were transfected. In the study, the regions of genomic DNA flanking the integrated expression vector were cloned and sequenced. Briefly, genomic DNA from the host cell was digested with XbaI, and fragments of an average size of approximately 5 kilobases (kb) were purified using a BioGel A-50 column basically as described by Reynaud et al. (*J. Mol. Biol.*, 140: 481-504 (1980)). A library of the purified genomic fragments was prepared by cloning the fragments into the lambda (λ) DASH® cloning vector (Stratagene, La Jolla, Calif.). The library was amplified and packaged using GIGAPACK® packaging extract (Stratagene) and transduced into XL1-Blue MRA or XL1-Blue MRA(P2) *Escherichia coli* cells according to the manufacturer's protocols. The library was then screened with probes for the coding sequence of the heavy chain variable region ($V_H$) of the anti-IL-12 antibody according to Stratagene protocols. A 14.5 kb Xba1 fragment in λDASH clone#21 contained the insertion site for the antibody expression vector along with flanking genomic sequences. These flanking genomic regions were designated ARM1 and ARM2. The sequences of ARM1 and ARM2 regions were determined to be that of SEQ ID NO:1 and SEQ ID NO:2, respectively. With respect to the insertion site of the antibody expression vector in the CHO cell genome, ARM1 is located upstream of the insertion site and 5' to the direction of transcription of the vector gene for the antibody heavy chain, and ARM2 is located downstream of the insertion site and 3' to the direction of transcription of the vector gene for the antibody light chain.

A BLAST analysis of SEQ ID NO:1 and SEQ ID NO:2 against a CHO expressed sequence tag (EST) data base failed to reveal any related coding sequences, suggesting that the ARM1 and ARM2 rEVE sequences do not contain any CHO coding sequences. A BLAST analysis of the rEVE sequences was also conducted against the mouse genome sequence. No mouse genomic sequence was identified that was homologous to the ARM1 sequence. However, the ARM2 sequence appears to be related to a highly conserved area on mouse chromosome 14 that contains no known coding sequences.

Using the Vector NTI sequence analysis program (Invitrogen), the sequences of ARM1 (SEQ ID NO:1) and ARM2 (SEQ ID NO:2) were also screened for the presence of a sampling of various representative (i.e., not all) nucleotide sequence motifs for matrix attachment region (MAR) elements (see, e.g., Michalowski et al., *Biochemistry*, 38: 12795-12804 (1999)). The specific MAR DNA sequence motifs screened by the computer program are shown in Table 1 (complementary strand sequences not listed).

TABLE 1

Nucleotide Sequence Motifs for Representative Matrix Attachment Region (MAR) Elements

| MAR Element | MAR Sequence Motif* Screened |
|---|---|
| A-Box | AATAAAYAA (SEQ ID NO: 3) (2 mismatches allowed) |
| T-Box | TTWTWTTWTT (SEQ ID NO: 4) (1 mismatch allowed) |
| MRS | TAWAWWWNNAWWRTAANNWWG (SEQ ID NO: 5) (2 mismatches allowed, but 3' terminus is G) or TAWAWWW (bases 1-7 of SEQ ID NO: 5) (first part of MRS, no mismatches) + AWWRTAANNWWG (bases 10-21 of SEQ ID NO: 5) (second part of MRS, 1 mismatch allowed, but 3' terminus is G), where first and second MRS parts counted with up to 4 intervening bases ($N_{14}$) or up to 3 overlapping bases |
| ARS | WTTTATRTTTW (SEQ ID NO: 6) (1 mismatch allowed) |
| BUR | AATATATTT (SEQ ID NO: 7) (1 mismatch allowed) |
| Curved | AAAANNNNNNNAAAANNNNNNNAAAA (SEQ ID NO: 8) or TTTAAA (SEQ ID NO: 9) |
| 90% AT | $W_{20}$ (SEQ ID NO: 10) (2 mismatches allowed) |
| Kinked | TANNNTGNNNCA (SEQ ID NO: 11) or TANNNCANNNTG (SEQ ID NO: 12) or TGNNNTANNNCA (SEQ ID NO: 13) or CANNNTANNNTG (SEQ ID NO: 14) (no mismatches allowed) |
| Topoisomerase II Binding Site | GTNWAYATTNATNNR (SEQ ID NO: 15) (2 mismatches allowed, but not in positions 4-9, i.e., WAYATT (bases 4-9 of SEQ ID NO: 15) conserved) |
| TG-Rich | CAAAACA (SEQ ID NO: 16) |
| DNA Unwinding Motif | AATATT (SEQ ID NO: 17) or AAATATT (SEQ ID NO: 18) |

*complementary strand sequences not listed; abbreviations: Y = T or C; W = A or T; N = A, T, G, or C; R = G or A As shown in Table 2, below, at least 41 MAR element sequences were identified in the ARM1 DNA sequence (SEQ ID NO:1) or its complementary strand sequence, and at least 114 MAR element sequences were identified in the ARM2 DNA sequence (SEQ ID NO:2) or its complementary strand sequence.

TABLE 2

Location of MAR Sequences in ARM1 and ARM2 DNA Sequences

| MAR Element | Location in ARM1 Sequence (bases of SEQ ID NO: 1)* | Location in ARM2 Sequence (bases of SEQ ID NO: 2)* |
|---|---|---|
| A-Box | 1756-1764, 1939-1947, 1975-1983, 2062-2070, 2072-2080, 2079-2087, 2216-2224, 2280-2288 | 52-60, 69-77, 79-87, 244-252 (complementary), 340-348 (complementary), 446-454 (complementary), 481-489 (complementary), 484-492 (complementary), 627-635, 631-639, 664-672 (complementary), 734-742, 737-745, 741-749, 811-819 (complementary), 821-829, 833-841, 840-848, 907-915 (complementary), 925-933 (complementary), 942-950 (complementary), 1104-1112 (complementary), 1186-1194 (complementary), 1186-1213 (cluster, complementary), 1262-1270 (complementary), 1391-1399, 1409-1417, 1413-1421, 1421-1429, 1441-1449 (complementary), 1531-1539 (complementary), 1711-1719 (complementary), 1715-1723 (complementary), 1740-1748, 1810-1818, 1817-1825, 1844-1852, 1848-1856, 1862-1870, 2036-2044 (complementary), 2040-2048 (complementary), 2052-2060, 2100-2108 (complementary), 2107-2115 (complementary), 2113-2121, 2118-2126, 2122-2130, 2191-2199 (complementary), 2261-2269 (complementary), 2287-2295 |
| T-Box | 114-145 (cluster), 1740-1752 (cluster), 2000-2011 (cluster), 2062-2087 (cluster) | 483-492, 631-640, 734-743, 806-815, 925-934, 1198-1207, 1843-1852 |
| MRS | 130-151, 1969-1989, 2054-2074, 2266-2286 | 77-97, 401-421, 752-772, 1197-1213 |
| ARS | 121-131, 2062-2072, 2079-2089, 2126-2136, 2257-2267 | 1443-1453 |
| BUR | 1877-1885, 2005-2013, 2063-2071, 2098-2106 (complementary), 2281-2289 | 77-85, 255-263, 723-731, 1412-1420 |
| Curved | 106-131, 2011-2016, 2293-2298 | 437-442, 466-471, 530-535, 616-621, 627-632, 2151-2156 |
| 90% AT | 106-125, 126-145 | 64-83, 64-90 (cluster), 243-263 (cluster), 400-420, 613-645 (cluster), 698-717, 722-774 (cluster), 805-845 (cluster), 1185-1214 (cluster), 1407-1431 (cluster), 2104-2136 (cluster) |
| Kinked | 860-871, 1761-1772 | 439-450, 671-682, 1124-1135, 1503-1514, 1967-1978, 2020-2031, 2058-2069 |
| Topoisomerase II Binding Site | 598-612, 1365-1382, 2042-2056 (complementary) | 720-734, 819-833 (complementary), 1251-1265, 1407-1421 (complementary), 1415-1429 (complementary), 1418-1432, 1434-1448 (complementary), 1758-1775, 1981-1995, 2202-2216 (complementary) |
| TG-Rich | 252-258 (complementary) | 928-936, 1842-1848 (complementary) |
| DNA Unwinding Motif | 1880-1885, 2021-2026, 2064-2069, 2066-2071 | 284-289, 415-420, 788-793, 789-794, 825-830, 826-831, 909-914, 1121-1126, 1421-1426, 1440-1446, 2208-2213, 2209-2214 |

*ARM1 sequence (SEQ ID NO: 1) or ARM2 sequence (SEQ ID NO: 2); "complementary" = complementary strand sequence; "cluster" = more than one copy of indicated MAR element in specified sequence The results of the MAR sequence analysis (which included complementary strand analysis) of ARM1 and ARM2 in Table 2 indicate that the various MARs are clustered predominantly in the 3' terminal portion of ARM1 (SEQ ID NO:1) and in both the 5' portion and 3' portion of ARM2 (SEQ ID NO:2). ARM1 has fewer of these MAR sites than ARM2. Moreover, the majority of the MAR sequences in ARM1 are in the 3' region of the sequence, whereas both the 5' and the 3' regions of ARM2 are populated by MAR sequences.

Example 2

General Protocols for Studies of the Affect of ARM1 and ARM2 rEVEs on Levels of Expression of Recombinant Proteins Cells for Expression Studies The DUXB11 CHO cell line is a CHO cell line that is deficient in expression of dihydrofolate reductase (DHFR$^-$) (see, Urlaub, G. and Chasin, L. A., *Proc. Natl. Acad. Sci. U.S.A.*, 77: 4216-4220 (1980)). The DHFR$^-$ phenotype of this cell line permits the use of a standard dihydrofolate reductase-methotrexate system (DHFR-MTX) protocol to amplify the copy number of an expression vector that has been transfected into these cells (see, e.g., Kaufman, R. J., In *Genetic Engineering: Principles and Methods* (ed. J. K. Setlow), volume 9, page 155 (Plenum Publishing, New York, 1987)).

Expression Vectors Containing ARM1 and ARM2 rEVE Sequences

Figure 2:
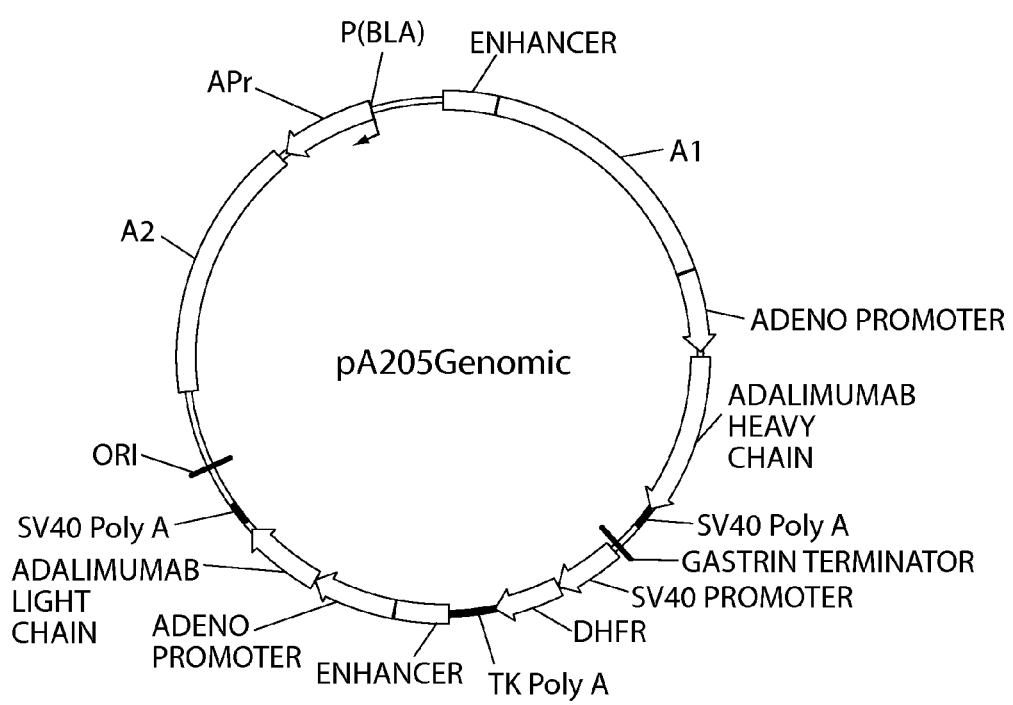
FIG. 2 is a schematic diagram of plasmid expression vector pA205Genomic in which ARM1 ("A1") nucleic acid that has the nucleotide base sequence of SEQ ID NO:1 is inserted into expression vector pA205 (FIG. 1) upstream of the adenovirus major late promoter and adalimumab IgG1 heavy chain coding region, and ARM2 ("A2") nucleic acid that has the nucleotide base sequence of SEQ ID NO:2 is inserted downstream of the adalimumab kappa light chain coding region. For other abbreviations, see the description of FIG. 1, above.
Figure 3:
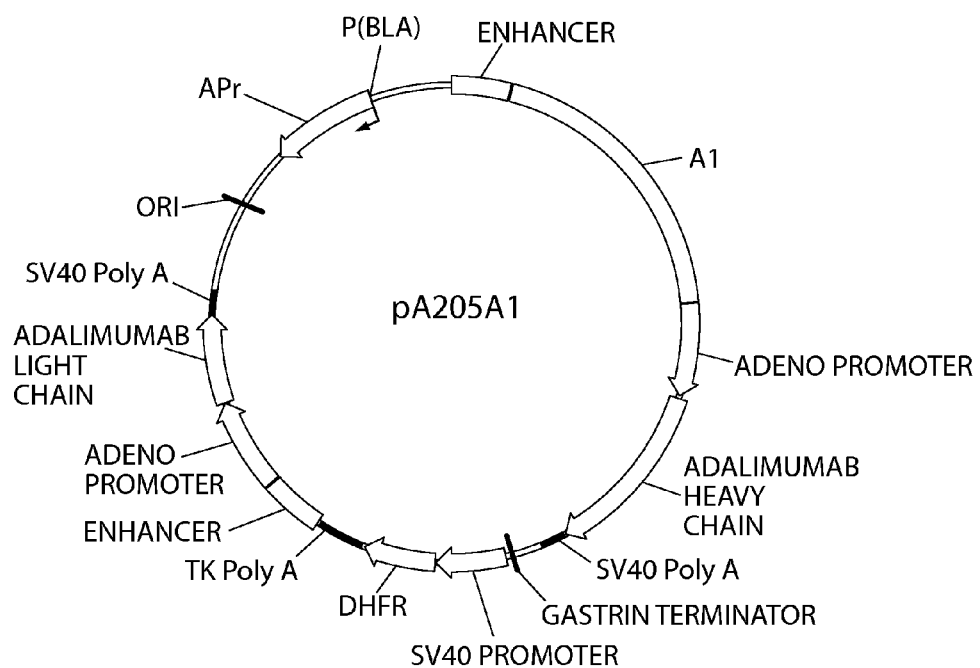
FIG. 3 is a schematic diagram of plasmid expression vector pA205A1 in which ARM1 ("A1") nucleic acid having the sequence of SEQ ID NO:1 is inserted into expression vector pA205 (FIG. 1) upstream of the adeno promoter and the adalimumab IgG1 heavy chain coding region. For other abbreviations, see the description of FIG. 1, above.
Figure 4:
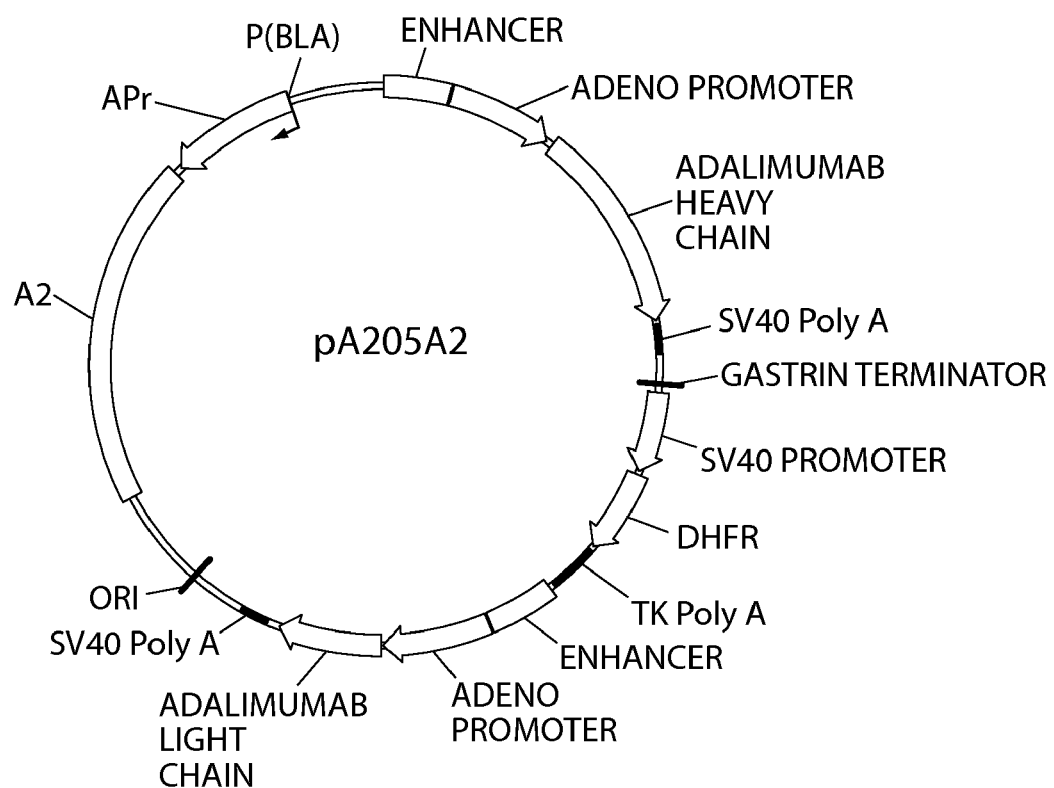
FIG. 4 is a schematic diagram of plasmid expression vector pA205A2 in which ARM2 ("A2") nucleic acid having the nucleotide base sequence of SEQ ID NO:2 is inserted downstream of the adalimumab kappa light chain coding region. For other abbreviations, see the description of FIG. 1, above.

FIG. 1 provides a schematic diagram of plasmid expression vector pA205. FIG. 2 provides a schematic diagram of plasmid expression vector pA205Genomic in which the genes encoding the heavy and light chains for adalimumab are flanked by ARM1 and ARM2 such that an ARM1 sequence is located upstream of the gene for the heavy chain of adalimumab and an ARM2 sequence is located downstream of the gene for the light chain of adalimumab. FIG. 3 provides a schematic diagram of plasmid expression vector pA205A1 in which an ARM1 sequence is located upstream of the gene for the heavy chain of adalimumab. FIG. 4 provides a schematic diagram of plasmid expression vector pA205A2 in which an ARM2 sequence is located downstream of the gene for the light chain of adalimumab.

Figure 5:
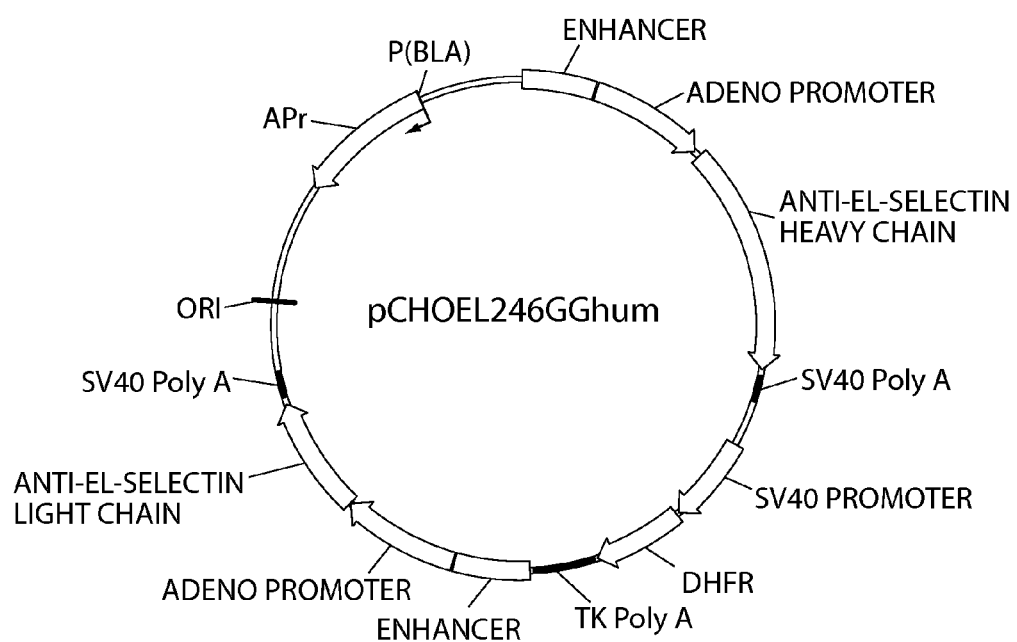
FIG. 5 is a schematic diagram of plasmid expression vector pCHOEL246GGhum used to express the immunoglobulin heavy and kappa light chains that form an active human anti-EL-selectin IgG1 molecule in stable transfectants of Chinese hamster ovary (CHO) cells. "ANTI-EL-SELECTIN HEAVY CHAIN" refers to the coding region for the heavy chain of a human anti-EL-selectin IgG1 antibody; "ANTI-EL-SELECTIN LIGHT CHAIN" refers to the coding region for the kappa light chain of a human anti-EL-selectin IgG1 antibody. For other abbreviations, see the description of FIG. 1, above.
Figure 6:
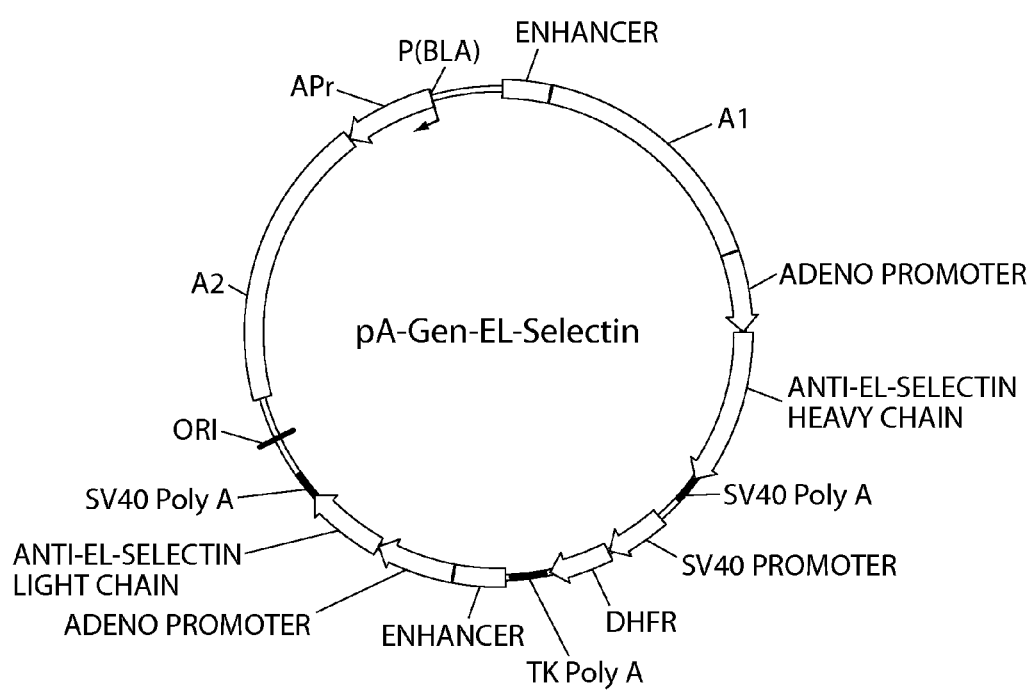
FIG. 6 is a schematic diagram of plasmid expression vector pA-Gen-EL-Selectin in which ARM1 ("A1") nucleic acid having the nucleotide base sequence of SEQ ID NO:1 is inserted into expression vector pCHOEL246GGhum (FIG. 5) upstream of the anti-EL-selectin IgG1 heavy chain coding region, and ARM2 ("A2") nucleic acid having the nucleotide base sequence of SEQ ID NO:2 is inserted downstream of the anti-EL-selectin kappa light chain coding region. For other abbreviations, see the description of FIG. 1, above.

FIG. 5 provides a schematic diagram of plasmid expression vector pCHOEL246GGhum, which contains the genes for the heavy and light chains of a human anti-EL-selectin antibody. FIG. 6 provides a schematic diagram of plasmid expression vector pA-Gen-EL-Selectin in which the genes encoding the heavy and light chains for the anti-EL-selectin antibody are flanked by ARM1 and ARM2 sequences such that an ARM1 sequence is located upstream of the gene for the antibody heavy chain and an ARM2 sequence is located downstream of the gene for the antibody light chain.

Figure 7:
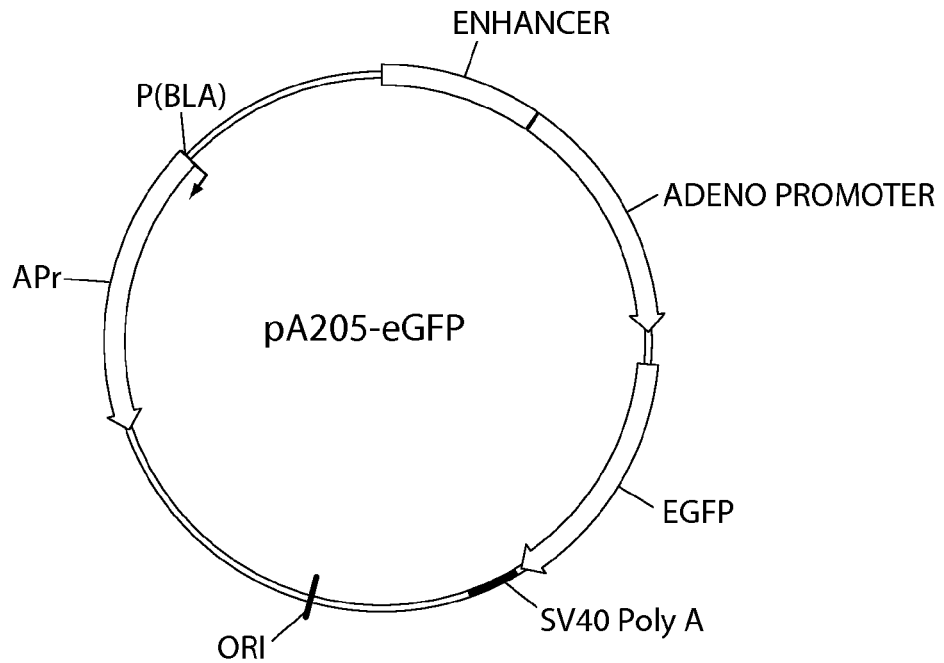
FIG. 7 is a schematic diagram of plasmid expression vector pA205-eGFP used to express enhanced green fluorescent protein (eGFP) in stable transfectants of CHO cells. The eGFP coding region ("EGFP") is inserted downstream from the adenovirus major late promoter ("ADENO PROMOTER") into pA205 (FIG. 1) from which the light chain coding region, proximal promoter, and proximal enhancer and the heavy chain coding region have been deleted. For other abbreviations, see the description of FIG. 1, above.
Figure 8:
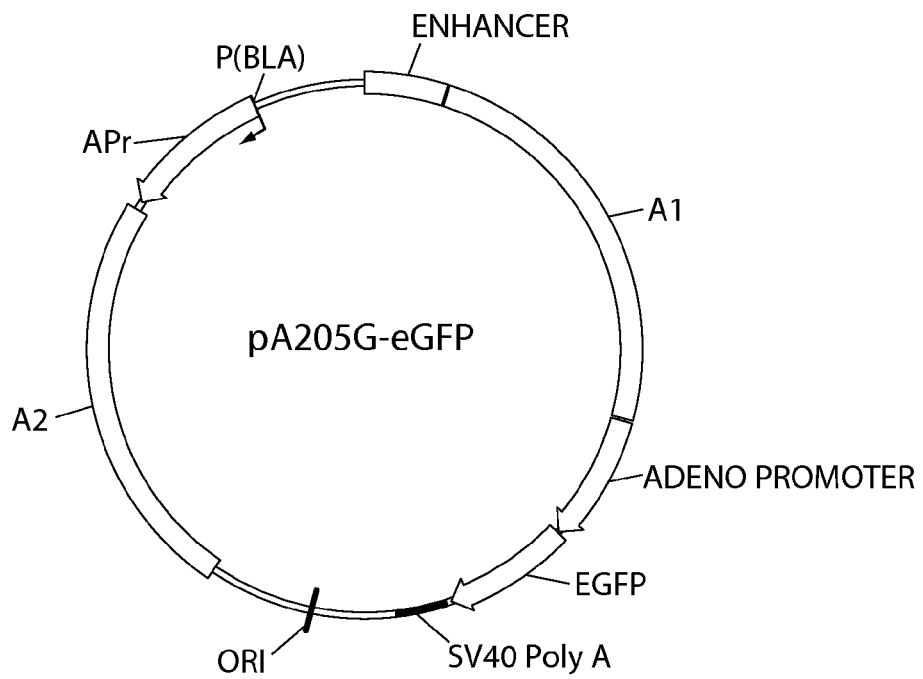
FIG. 8 is a schematic diagram of plasmid expression vector pA205G-eGFP in which ARM1 ("A1") nucleic acid having the nucleotide base sequence of SEQ ID NO:1 is inserted into expression vector pA205-eGFP (FIG. 7) upstream of the eGFP coding region ("EGFP"), and ARM2 ("A2") nucleic acid having the nucleotide base sequence of SEQ ID NO:2 is inserted downstream of the eGFP coding sequence. For other abbreviations, see the description of FIG. 1, above.

FIG. 7 provides a schematic diagram of plasmid expression vector pA205-eGFP, which contains the gene for enhanced Green Fluorescent Protein (eGFP). FIG. 8 provides a schematic diagram of plasmid expression vector pA205G-eGFP in which the gene encoding the enhanced Green Fluorescent Protein is flanked by ARM1 and ARM2 sequences such that the ARM1 sequence is located upstream of the gene for eGFP and the ARM2 sequence is located downstream of the eGFP gene.

Figure 9:
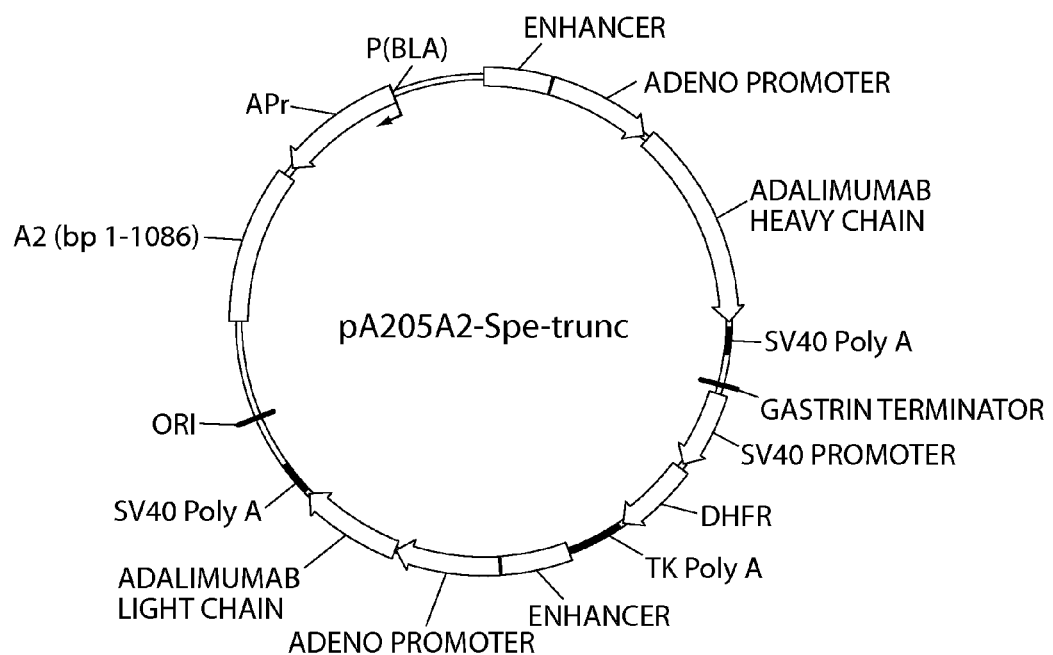
FIG. 9 is a schematic diagram of plasmid expression vector pA205A2-Spe-trunc, which is essentially identical to expression vector pA205A2 shown in FIG. 4, except that the ARM2 (SEQ ID NO:2) has been replaced with a truncated ARM2 variant, "A2 (bp 1-1086)", which has the nucleotide base sequence of bases 1-1086 of SEQ ID NO:2 as the result of digestion of ARM2 nucleic acid with restriction endonuclease SpeI. For other abbreviations, see the description of FIG. 1, above.
Figure 10:
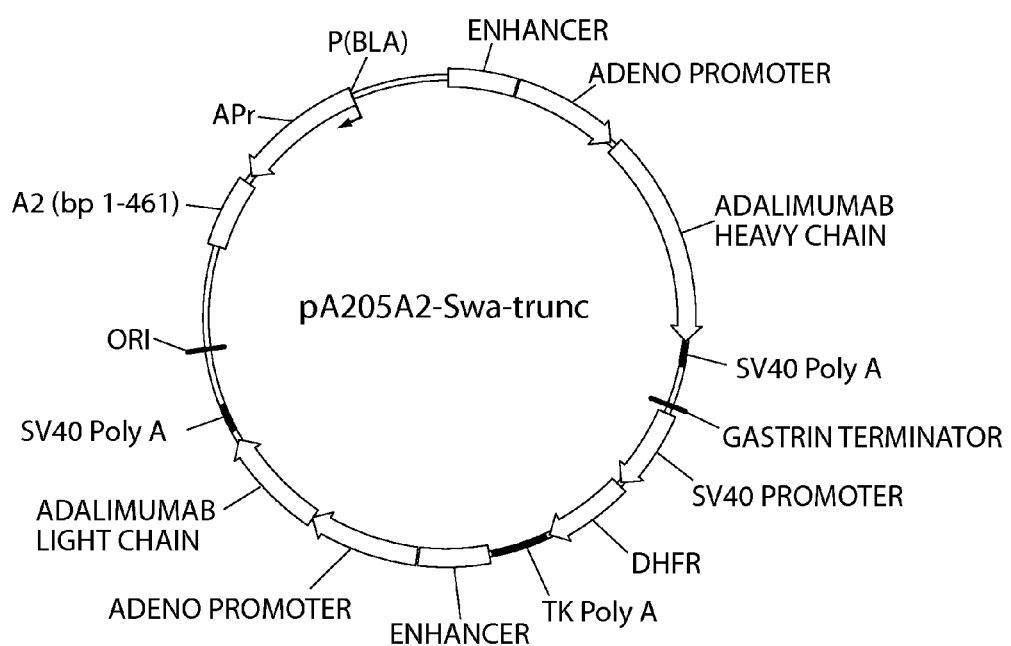
FIG. 10 is a schematic diagram of plasmid expression vector pA205A2-Swa-trunc, which is essentially identical to expression vector pA205A2 shown in FIG. 4, except that ARM2 (SEQ ID NO:2) has been replaced with a truncated ARM2 variant, "A2 (bp 1-461)", which has the nucleotide base sequence of bases 1-461 of SEQ ID NO:2 as the result of digestion of ARM2 nucleic acid with restriction endonuclease Swa1. For other abbreviations, see the description of FIG. 1, above.

FIG. 9 provides a schematic diagram of plasmid expression vector pA205A2-Spe-trunc, which is essentially identical to expression vector pA205A2 shown in FIG. 4, except that the ARM2 sequence has been replaced with a truncated ARM2 variant, "A2 (bp 1-1086)", which has the nucleic acid base sequence of bases 1-1086 of SEQ ID NO:2 as the result of digestion of ARM2 DNA with restriction endonuclease SpeI. FIG. 10 provides a schematic diagram of plasmid expression vector pA205A2-Swa-trunc, which is essentially identical to expression vector pA205A2 shown in FIG. 4, except that the ARM2 sequence has been replaced with a truncated ARM2 variant, "A2 (bp 1-461)", which has the nucleic acid base sequence of bases 1-461 of SEQ ID NO:2 as the result of digestion of ARM2 DNA with restriction endonuclease SwaI.

Culture Media

αMEM is minimal essential medium, α medium (GIBCO®, Invitrogen, Carlsbad, Calif.).

Growth of Cells and Transfections

Three 10 cm tissue culture plates per transfection were seeded with $1\times10^6$ B3.2 parental DUXB11 CHO cells each in 10 ml of αMEM supplemented with 5% dialyzed FBS and H/T (GIBCO). These cells were transfected eighteen hours (18 h) later in accordance with the calcium phosphate transfection protocol described in *Current Protocols in Molecular Biology*, (Ausubel, F. V., Brent, R., Moore, D. M., Kingston, R. E., Seidman, J. G., Smith, J. A., and K. Struhl eds.), (Wiley Interscience, New York, 1990)) with several modifications as indicated, below. Growth medium was removed from culture plates by aspiration, and 9 ml of Ham's F12 medium (Invitrogen) was added to each plate. The plates were incubated at 37° C. for two hours prior to transfection.

Calcium Phosphate Transfection Protocol

Seventy-five micrograms (75 µg) of DNA were dissolved in 1.35 ml water in a 50 ml conical tube. One hundred and fifty microliters (150 µl) of 2.5 M CaCl$_2$ were added, and this DNA-calcium mixture was added dropwise to 1.5 ml of 2× HeBES (HEPES buffered saline) in a 50 ml conical tube. The HeBES was bubbled with a pipettor while adding the DNA-calcium mixture with a Pasteur pipette. The mixture was mixed by vortex for 5 seconds and incubated at room temperature for 20 minutes. One milliliter (1 ml) of the DNA-calcium mixture was distributed evenly over each culture dish of adherent cells, grown and prepared for transfection in F12 medium as described above, and the cultures then incubated at 37° C. for four hours. After incubation, the plates were aspirated, and 2 ml of 10% dimethylsulfoxide (DMSO) in F12 medium was added to each plate (DMSO shock treatment). The DMSO shock continued for one minute after which the DMSO was diluted by the addition of 5 ml of PBS (phosphate buffered saline) to each plate. The plates were aspirated and washed two more times in PBS. Ten (10) ml of αMEM/5% FBS/HT was added, and the plates were incubated at 37° C. overnight.

Seeding of Transfected Cells into 96-Well Plates and Methotrexate (MTX) Amplification The next day, the cells were seeded into 96-well plates as follows: The cells from all of the 10 cm plates were harvested by trypsin digestion and resuspended at a density of 2000 cells/ml in αMEM/5% FBS. Ninety-six 96-well plates were seeded at 10 ml/plate, 100 µl/well. The medium was changed on the 96-well plates one week later, two weeks later, and again five days after that. The medium αMEM/5% FBS used was selective for cells expressing DHFR.

Two days after the last medium change, the culture supernatants were diluted 1:40 and tested using an ELISA specific for human IgG gamma chain to detect expression of adalimumab or anti-EL-selectin antibody. The clones which gave the highest ELISA signal were transferred from their 96-well plates into 12-well plates in 2.0 ml/well of αMEM/5% FBS. When confluent (approximately 2-5 days later), these were assayed again, and clones were split into the same medium+

20 nM MTX for amplification. Cells were initially selected in αMEM/5% FBS and 20 nM MTX in a 12-well tissue culture plate. These cells, after initial selection at this MTX level were passed a minimum of two more times in growth medium containing 20 nM MTX over an average period of eighteen days. The cell lines were amplified then to 100 nM MTX. During this period of culture, the adalimumab (human anti-TNF-α antibody) or anti-EL-Selectin productivity of the cultures increased. After selection at 100 nM MTX level, the lines were passed a minimum of two more times in growth medium containing 100 nM MTX over an average period of eighteen (18) days. Where indicated, the cell lines were further amplified to 500 nM MTX. After selection at 500 nM MTX level, the lines were passed a minimum of two more times in growth medium containing 500 nM MTX over an average period of eighteen (18) days.

Cultures of transfected CHO cells carrying expression vectors comprising an ARM1 nucleic acid sequence (SEQ ID NO:1), an ARM2 nucleic acid sequence (SEQ ID NO:2), or a combination of ARM1 and ARM2 sequences, adapt better, i.e., have higher survivability and/or higher growth rates, in the presence of methotrexate compared to CHO cells transfected with the same expression vectors lacking these rEVE sequences.

Example 3

Effect of ARM1 and ARM2 Sequences on Levels of Expression of Anti-TNF-α in Transfected CHO Cells In this study, the effect of ARM1 and ARM2 sequences on the expression of a human anti-TNF-α antibody (adalimumab) in stably transfected CHO cells was examined. The levels of expression of adalimumab were compared in CHO cells stably transfected with expression vector pA205 (no ARM sequences), pA205Genomic (containing both ARM1 and ARM2), pA205A1 (containing ARM1), or pA205A2 (containing ARM2). Table 3 shows the average level of production of adalimumab in adherent cultures of the top three producing clones from each vector transfection at the indicated amplification level (concentration of methotrexate, "MTX").

TABLE 3

Level of Adalimumab Expression in Stably Transfected CHO Cells

| Vector | 0 nM MTX | 20 nM MTX | 100 nM MTX |
|---|---|---|---|
| pA205 | 1.57 µg/ml | 4.20 µg/ml | 5.53 µg/ml |
| pA205Genomic | 4.60 µg/ml | 14.80 µg/ml | 21.03 µg/ml |
| pA205A1 | 3.13 µg/ml | 9.90 µg/ml | 17.3 µg/ml |
| pA205A2 | 4.53 µg/ml | 24.23 µg/ml | 20.8 µg/ml |

The data in Table 3 indicate that ARM1 and ARM2 sequences, alone or in combination, enhanced the level of expression of adalimumab compared to that seen in cells transfected with a vector lacking ARM sequences (pA205). Overall, ARM2 alone (p205A2) provided the greatest level of enhanced expression relative to all other transfectants, whereas ARM1 alone (p205A1) provided the lowest of enhanced levels of expression. The data show that an isolated nucleic acid molecule that has the ARM1 sequence (SEQ ID NO:1) or ARM2 sequence (SEQ ID NO:2) is a representative recombinant expression vector element (rEVE), which when inserted into an expression vector can enhance expression of a recombinant protein encoded by and expressed from the expression vector.

The levels of expression of adalimumab by individual clones of the above-mentioned vector transfections were also compared after 1 week and 4 weeks in suspension cultures in the absence of methotrexate amplification. Results are shown in Table 4.

TABLE 4

Level of Adalimumab Expression in Suspension Cultures of Individual Clones of Stably Transfected CHO Cells after Week 1 and 4 in the Absence of Methotrexate

| Vector | Clone # | Week 1 (µg/ml) | Week 4 (µg/ml) |
|---|---|---|---|
| pA205 | 19-3 | 10.8 | 8.1 |
| pA205Genomic | 7-5 | 52.6 | 46.0 |
| | 14-6 | 19.9 | 16.8 |
| pA205A1 | 1-4 | 15.5 | 6.9 |
| | 4-2 | 27.8 | 15.3 |
| | 6-3 | 76.8 | 43.6 |
| | 3-7 | 17.3 | 12.6 |
| pA205A2 | 13-1 | 97.7 | 107.8 |
| | 9-7 | 63.7 | 64.9 |
| | 7-2 | 42.3 | 60.2 |
| | 5-3 | 180.4 | 153.0 |

The data in Table 4 show that incorporating ARM2 into pA205 without ARM1 (pA205A2) increases the stability of enhanced adalimumab expression levels over time. In particular, with both ARM1 and ARM2 present (pA205Genomic) or ARM1 alone (pA205A1), an enhanced level of expression of adalimumab was initially observed in cultures, but that level could quickly fall over a matter of weeks to much lower levels (see, Table 4). In contrast, in cultures of cells expressing adalimumab in the presence of ARM2 alone (pA205A2), the enhanced level of expression of adalimumab was stably maintained in three out of four cultures over the course of the 4 week period. Thus, ARM2 can stably maintain a significant elevation in the level of expression of adalimumab in suspension cultures of transfected CHO cells.

Example 4

Effect of ARM1 and ARM2 Sequences on the Level of Expression of Anti-EL-Selectin Antibody in Transfected CHO Cells In this study, the effect of ARM1 and ARM2 sequences on the expression of a human anti-EL-selectin antibody (which binds E- and L-selectins) in stably transfected CHO cells was examined. The levels of expression of this anti-selectin antibody were compared in CHO cells stably transfected with expression vector pCHOEL246GGhum (no ARM sequences) or with expression vector pA-Gen-EL-Selectin (containing both ARM1 and ARM2). Table 5 shows the average level of production of the anti-selectin antibody in adherent cultures of the top three producing clones from each vector transfection at the indicated amplification level (concentration of methotrexate, "MTX").

TABLE 5

Level of Anti-EL-Selectin Antibody Expression in Stably Transfected CHO Cells

| Vector | 0 nM MTX | 20 nM MTX | 100 nM MTX | 500 nM MTX |
|---|---|---|---|---|
| pCHOEL246GGhum | 7.93 µg/ml | 15.47 µg/ml | 17.27 µg/ml | 22.30 µg/ml |
| pA-Gen-EL-Selectin | 6.27 µg/ml | 19.87 µg/ml | 26.63 µg/ml | 44.13 µg/ml |

The data in Table 5 show that ARM1 and ARM2 sequences (pAGen-EL-Selectin) were effective in elevating the level of expression of anti-EL-selectin antibody in methotrexate-amplified cultures of stably transfected CHO cells.

Example 5

Effect of ARM1 and ARM2 Sequences on Levels of Expression of Enhanced Green Fluorescent Protein (eGFP) in Transfected Cho Cells Constructs containing a gene encoding enhanced green fluorescent protein (eGFP) were transfected into CHO cells as described above with the exception that the cells were co-transfected with pcDNA3.1-hygro to provide a selectable marker, i.e., hygromycin resistance, for stable transfectants. Expression vector peGFP provides a positive control for expression of eGFP under the transcriptional control of a CMV promoter. Plasmid pA205-eGFP contains the eGFP gene on the pA205 expression vector without ARM1 or ARM2 sequences (FIG. 7). Plasmid pA205Gen-eGFP (FIG. 8) contains both ARM1 and ARM2 flanking the gene encoding eGFP. There is no DHFR selection gene in either of these plasmids. Accordingly, no DHFR-methotrexate amplification steps were taken. Transfectants were selected with hygromycin at a concentration of 400 µg/ml for 2 weeks, splitting when necessary, and then sorted by FACS to determine expression levels. The cells were originally sorted into pools for each type of vector, and expressing cells were grown for an additional two weeks, then resorted.

TABLE 6

Level of eGFP Expression in Stably Transfected CHO Cells

| Vector | Mean Fluorescence Units |
|---|---|
| peGFP (positive control) | 239.03 |
| pA205-eGFP | 17.36 |
| pA205Gen-EGFP | 104.86 |

The data in Table 6 indicate that ARM1 and ARM2 sequences were effective at significantly enhancing the level of expression of eGFP in transfected CHO cells compared to the level of expression in cells transfected with the same eGFP expression vector, but lacking ARM sequences (pA205-eGFP).

Example 6

Effect of Deletion Mutants of ARM2 on Levels of Expression of Adalimumab in Transfected CHO Cells The 3' terminal region of the ARM2 sequence (SEQ ID NO:2) was truncated in pA205A2 vector to either the SpeI cleavage site (at base 1086 of SEQ ID NO:2) or the SwaI cleavage site (at base 461 of SEQ ID NO: 2) to create, respectively, pA205A2-Spe-trunc (containing the sequence of bases 1-1086 of SEQ ID NO:2) and pA205A2-Swa-trunc (containing the sequence of bases 1-461 of SEQ ID NO:2). The resulting plasmids were transfected into CHO cells as described above and amplified to 20 nM MTX. Table 7 shows the average level of expression in adherent cultures of the top three producing clones from each transfection at each amplification level.

TABLE 7

Level of Adalimumab Expression in Stably Transfected CHO Cells

| Vector | 0 nM MTX | 20 nM MTX |
|---|---|---|
| pA205 | 1.80 µg/ml | 1.57 µg/ml |
| pA205A2 | 6.10 µg/ml | 15.73 µg/ml |
| pA205A2-Spe-trunc | 3.57 µg/ml | 3.00 µg/ml |
| pA205A2-Swa-trunc | 0.83 µg/ml | 0.90 µg/ml |

The data in Table 7 show that CHO cells transfected with expression vector pA205A2-Spe-trunc, which contains the 5' terminal 1086 base pairs of the ARM2 DNA, produced adalimumab at a lower level of enhanced expression compared to CHO cells transfected with the pA205A2 vector. Surprisingly, cells transfected with expression vector pA205A2-Swa-trunc, which contains the 5' terminal 461 base pairs of the ARM2 DNA, produced adalimumab at even lower levels of expression than cells transfected with pA205, which contains no ARM sequence. The data in Table 7 indicate that the regions deleted from the 3' terminus of the ARM2 DNA are of special interest for enhanced expression of recombinant proteins in host cells. In addition, the presence of a relatively small, i.e., 461 base pair, 5' terminal fragment of ARM2 DNA, alone, actually appears to reduce expression of recombinant gene product in transfected host cells and may be particularly useful in substantially lowering or silencing expression of a recombinant gene product. Such an application may be desired when expression of a gene product would be toxic or otherwise undesired in a host cell, e.g., under certain culture conditions.

Example 7

Expression Levels of Individual Transfectants from the Preceding Studies

The tables shown below provide the level of expression of recombinant proteins produced by individual transfected clones generated in the preceding studies.

TABLE 8

Levels of Adalimumab Expression in CHO Cells Transfected with pA205

| pA205 clone# | 0 nM MTX | 20 nM MTX | 100 nM MTX | 500 nM MTX |
|---|---|---|---|---|
| 1 | 3.9 | 10.4 | 15.4 | 14.1 |
| 2 | 2.8 | 6.2 | 12.9 | 8.2 |

TABLE 8-continued

Levels of Adalimumab Expression in CHO Cells Transfected with pA205

| pA205 clone# | 0 nM MTX | 20 nM MTX | 100 nM MTX | 500 nM MTX |
|---|---|---|---|---|
| 3 | 2.50 | 4.2 | 10.1 | 2.9 |
| 4 | 2.1 | 3.8 | 4.2 | 1.5 |
| 5 | 1.7 | 2.7 | 2.9 | 0.3 |
| 6 | 1.4 | 2.2 | 2.6 | |
| 7 | 1.4 | 1.7 | 2 | |
| 8 | 1.3 | 1.6 | 1.7 | |
| 9 | 1.3 | 1.6 | 1.4 | |
| 10 | 1.2 | 1.6 | 1.4 | |
| 11 | 1.10 | 1.4 | 1 | |
| 12 | 1.10 | 1.3 | 0.8 | |
| 13 | 1 | 1.3 | 0.5 | |
| 14 | 1.00 | 1.3 | 0 | |
| 15 | 0.9 | 1.2 | | |
| 16 | 0.90 | 1.2 | | |
| 17 | 0.9 | 1.1 | | |
| 18 | 0.9 | 1.1 | | |
| 19 | 0.9 | 1.01 | | |
| 20 | 0.9 | 0.9 | | |
| 21 | 0.80 | 0.8 | | |
| 22 | 0.8 | 0.8 | | |
| 23 | 0.8 | 0.7 | | |
| 24 | 0.70 | 0.7 | | |
| 25 | 0.70 | 0.6 | | |
| 26 | 0.7 | 0.6 | | |
| 27 | 0.7 | 0.3 | | |
| 28 | 0.5 | 0.1 | | |
| 29 | 0.50 | 0.09 | | |
| 30 | 0.50 | 0.08 | | |
| 31 | 0.5 | 0.07 | | |
| 32 | 0.5 | 0 | | |
| 33 | 0.5 | 0 | | |
| 34 | 0.4 | 0 | | |
| 35 | 0.4 | 0 | | |
| 36 | 0.40 | 0 | | |
| 37 | 0.40 | 0 | | |
| 38 | 0.40 | 0 | | |
| 39 | 0.40 | 0 | | |
| 40 | 0.4 | 0 | | |
| 41 | 0.4 | 0 | | |
| 42 | 0.3 | 0 | | |
| 43 | 0.3 | | | |
| 44 | 0.30 | | | |
| 45 | 0.3 | | | |
| 46 | 0.3 | | | |
| 47 | 0.2 | | | |
| 48 | 0.20 | | | |
| 49 | 0.2 | | | |
| 50 | 0.2 | | | |
| 51 | 0.1 | | | |
| 52 | 0.1 | | | |
| 53 | 0.1 | | | |
| 54 | 0.1 | | | |
| 55 | 0.10 | | | |
| 56 | 0.10 | | | |
| 57 | 0.10 | | | |
| 58 | 0.1 | | | |
| 59 | 0.08 | | | |
| 60 | 0.05 | | | |
| 61 | 0.05 | | | |
| 62 | 0.03 | | | |
| 63 | 0.03 | | | |
| 64 | 0.03 | | | |
| 65 | 0.02 | | | |
| 66 | 0.01 | | | |
| 67 | 0.01 | | | |
| 68 | 0.01 | | | |
| 69 | 0.01 | | | |
| 70 | 0.01 | | | |
| 71 | 0.009 | | | |
| 72 | 0.007 | | | |
| 73 | 0.007 | | | |
| 74 | 0.007 | | | |
| 75 | 0.006 | | | |
| 76 | 0 | | | |
| 77 | 0 | | | |
| 78 | 0 | | | |

TABLE 9

Levels of Adalimumab Expression in CHO Cells Transfected with pA205Genomic

| pA205Genomic clone# | 0 nM MTX | 20 nM MTX | 100 nM MTX | 500 nM MTX |
|---|---|---|---|---|
| 1 | 9.3 | 19.1 | 61.0 | 40.6 |
| 2 | 6.9 | 16.5 | 59.7 | 40.2 |
| 3 | 6.5 | 15.1 | 52.0 | 28.6 |
| 4 | 5.70 | 13.6 | 36.0 | 23.9 |
| 5 | 5.6 | 13.2 | 25.9 | |
| 6 | 4.6 | 10.7 | 20.7 | |
| 7 | 4.3 | 10.3 | 19.6 | |
| 8 | 4.1 | 9.8 | 17.6 | |
| 9 | 4.10 | 9.7 | 16.3 | |
| 10 | 4.00 | 9.5 | 15.6 | |
| 11 | 3.9 | 8.9 | 11.4 | |
| 12 | 3.6 | 7.6 | 9.3 | |
| 13 | 3.5 | 6.9 | 8.1 | |
| 14 | 3.4 | 6.4 | 8 | |
| 15 | 3.3 | 6 | 5.9 | |
| 16 | 2.9 | 4.5 | 0.1 | |
| 17 | 2.9 | 3.1 | 0.04 | |
| 18 | 2.70 | 2.5 | | |
| 19 | 2.60 | 2.4 | | |
| 20 | 2.5 | 1.6 | | |
| 21 | 2.4 | 1.4 | | |
| 22 | 2.2 | 1.1 | | |
| 23 | 2.2 | 0.05 | | |
| 24 | 2.2 | 0 | | |
| 25 | 2.20 | 0 | | |
| 26 | 2 | | | |
| 27 | 2 | | | |
| 28 | 1.90 | | | |
| 29 | 1.90 | | | |
| 30 | 1.8 | | | |
| 31 | 1.80 | | | |
| 32 | 1.7 | | | |
| 33 | 1.7 | | | |
| 34 | 1.6 | | | |
| 35 | 1.6 | | | |
| 36 | 1.6 | | | |
| 37 | 1.50 | | | |
| 38 | 1.4 | | | |
| 39 | 1.4 | | | |
| 40 | 1.40 | | | |
| 41 | 1.3 | | | |
| 42 | 1.3 | | | |
| 43 | 1.30 | | | |
| 44 | 1.30 | | | |
| 45 | 1.2 | | | |
| 46 | 1.1 | | | |
| 47 | 1.1 | | | |
| 48 | 1.1 | | | |
| 49 | 1 | | | |
| 50 | 1.00 | | | |
| 51 | 0.80 | | | |
| 52 | 0.7 | | | |
| 53 | 0.7 | | | |
| 54 | 0.7 | | | |
| 55 | 0.6 | | | |
| 56 | 0.60 | | | |
| 57 | 0.5 | | | |
| 58 | 0.5 | | | |
| 59 | 0.5 | | | |
| 60 | 0.5 | | | |

TABLE 9-continued

Levels of Adalimumab Expression in CHO Cells Transfected with pA205Genomic

| pA205Genomic clone# | 0 nM MTX | 20 nM MTX | 100 nM MTX | 500 nM MTX |
|---|---|---|---|---|
| 61 | 0.5 | | | |
| 62 | 0.5 | | | |
| 63 | 0.4 | | | |
| 64 | 0.4 | | | |
| 65 | 0.4 | | | |
| 66 | 0.3 | | | |
| 67 | 0.3 | | | |
| 68 | 0.3 | | | |
| 69 | 0.3 | | | |
| 70 | 0.2 | | | |
| 71 | 0.2 | | | |
| 72 | 0.2 | | | |
| 73 | 0.2 | | | |
| 74 | 0.20 | | | |
| 75 | 0.1 | | | |
| 76 | 0.1 | | | |
| 77 | 0.04 | | | |
| 78 | 0 | | | |

TABLE 10

Levels of Adalimumab Expression in CHO Cells Transfected with pA205A1

| pA205A1 clone# | 0 nM MTX | 20 nM MTX | 100 nM MTX |
|---|---|---|---|
| 1 | 4.50 | 11.5 | 18.9 |
| 2 | 2.50 | 9.2 | 17.4 |
| 3 | 2.40 | 9 | 15.6 |
| 4 | 2.10 | 7.4 | 11.4 |
| 5 | 2.00 | 6.9 | 10.8 |
| 6 | 2.00 | 5.8 | 10.6 |
| 7 | 1.90 | 5.6 | 8.6 |
| 8 | 1.40 | 5.4 | 7.8 |
| 9 | 1.40 | 5.3 | 7.1 |
| 10 | 1.20 | 4.8 | 5.9 |
| 11 | 1.20 | 4.2 | 5.5 |
| 12 | 0.90 | 3.6 | 3.2 |
| 13 | 0.80 | 2.7 | 0.6 |
| 14 | 0.70 | 1.8 | 0.5 |
| 15 | 0.50 | 1.3 | |
| 16 | 0.40 | 0.6 | |
| 17 | 0.30 | 0.6 | |
| 18 | 0.07 | 0.05 | |
| 19 | 0.00 | 0.03 | |
| 20 | 0.00 | 0 | |

TABLE 11

Levels of Adalimumab Expression in CHO Cells Transfected with pA205A2

| pA205A2 clone# | 0 nM MTX | 20 nM MTX | 100 nM MTX |
|---|---|---|---|
| 1 | 9.4 | 32.4 | 26.8 |
| 2 | 6.0 | 21.5 | 17.9 |
| 3 | 4.80 | 21.2 | 17.7 |
| 4 | 4.60 | 19.1 | 15 |
| 5 | 4.20 | 18.6 | 13.2 |
| 6 | 3.70 | 16.6 | 12 |
| 7 | 3.50 | 13.9 | 7.6 |
| 8 | 3.50 | 13.4 | 6.5 |
| 9 | 3.20 | 12.3 | 5.2 |
| 10 | 3.0 | 11.4 | 4.8 |
| 11 | 2.8 | 11.2 | 4.6 |
| 12 | 2.7 | 10.4 | 4.2 |
| 13 | 2.60 | 9.6 | 2.6 |
| 14 | 2.60 | 9.4 | 2 |
| 15 | 2.50 | 9.2 | 1.6 |
| 16 | 2.5 | 8.5 | 0.01 |
| 17 | 2.40 | 7.5 | |
| 18 | 2.4 | 6.7 | |
| 19 | 2.30 | 5.3 | |
| 20 | 2.30 | 5 | |
| 21 | 2.3 | 4.9 | |
| 22 | 2.3 | 4.8 | |
| 23 | 2.20 | 4.2 | |
| 24 | 1.90 | 3.6 | |
| 25 | 1.8 | 2.6 | |
| 26 | 1.8 | 2.4 | |
| 27 | 1.70 | 2.3 | |
| 28 | 1.6 | 1.8 | |
| 29 | 1.5 | 1.6 | |
| 30 | 1.40 | 1.5 | |
| 31 | 0.8 | 1.2 | |
| 32 | 0.8 | 1.1 | |
| 33 | 0.7 | 0.8 | |
| 34 | 0.6 | 0.7 | |
| 35 | 0.6 | 0.3 | |
| 36 | 0.5 | 0.3 | |
| 37 | 0.5 | 0.05 | |
| 38 | 0.40 | 0 | |
| 39 | 0.3 | 0 | |
| 40 | 0.2 | 0 | |
| 41 | 0.1 | | |
| 42 | 0.1 | | |
| 43 | 0.07 | | |
| 44 | 0.05 | | |
| 45 | 0.05 | | |
| 46 | 0.00 | | |
| 47 | 0 | | |

TABLE 12

Levels of Adalimumab Expression in CHO Cells Transfected with pA205A2-Spe-trunc

| pA205A2-Spe-trunc clone# | 0 nM MTX | 20 nM MTX |
|---|---|---|
| 1 | 5.5 | 4.7 |
| 2 | 3.1 | 2.3 |
| 3 | 2.1 | 2.0 |
| 4 | 2 | 2.0 |
| 5 | 1.3 | 1.9 |
| 6 | 1.2 | 1.8 |
| 7 | 1.1 | 1.4 |
| 8 | 1.1 | 1.2 |
| 9 | 1 | 1.0 |
| 10 | 0.9 | 0.8 |
| 11 | 0.9 | 0.4 |
| 12 | 0.9 | 0.2 |
| 13 | 0.8 | 0 |
| 14 | 0.7 | 0 |
| 15 | 0.7 | 0 |
| 16 | 0.7 | |
| 17 | 0.6 | |
| 18 | 0.5 | |
| 19 | 0.4 | |
| 20 | 0.4 | |
| 21 | 0.4 | |
| 22 | 0.4 | |
| 23 | 0.4 | |
| 24 | 0.3 | |
| 25 | 0.2 | |
| 26 | 0.2 | |

TABLE 13

Levels of Adalimumab Expression in CHO Cells Transfected with pA205A2-Swa-trunc

| pA205A2-Swa-trunc clone# | 0 nM MTX | 20 nM MTX |
|---|---|---|
| 1 | 1.1 | 1.1 |
| 2 | 0.7 | 0.8 |
| 3 | 0.7 | 0.8 |
| 4 | 0.6 | 0.7 |
| 5 | 0.6 | 0.5 |
| 6 | 0.5 | 0.4 |
| 7 | 0.5 | 0.4 |
| 8 | 0.4 | 0.4 |
| 9 | 0.4 | 0.4 |
| 10 | 0.3 | 0.4 |
| 11 | 0.3 | 0.4 |
| 12 | 0.3 | 0.2 |
| 13 | 0.3 | 0.05 |
| 14 | 0.3 | 0 |
| 15 | 0.3 | 0 |
| 16 | 0.3 | 0 |
| 17 | 0.3 | |
| 18 | 0.2 | |
| 19 | 0.2 | |
| 20 | 0.2 | |
| 21 | 0.2 | |
| 22 | 0.2 | |
| 23 | 0.2 | |
| 24 | 0.1 | |
| 25 | 0.1 | |
| 26 | 0.1 | |
| 27 | 0.08 | |
| 28 | 0 | |

TABLE 14

Levels of Anti-EL-Selection Antibody Expression in CHO Cells Transfected with pCHOEL246GGhum

| pCHOEL246GGhum clone# | 0 nM MTX | 20 nM MTX | 100 nM MTX | 500 nM MTX |
|---|---|---|---|---|
| 1 | 14.4 | 24.4 | 22.9 | 32.8 |
| 2 | 5.5 | 11.7 | 15.4 | 20.2 |
| 3 | 3.9 | 10.3 | 13.5 | 13.9 |
| 4 | 2.3 | 8.5 | 9.8 | 10.5 |
| 5 | 2.3 | 7.1 | 8.5 | 8.2 |
| 6 | 2.3 | 6.7 | 6.2 | 7.7 |
| 7 | 1.7 | 6.5 | 5.4 | 7.4 |
| 8 | 1.6 | 5.8 | 4.4 | 5.4 |
| 9 | 1.6 | 4.9 | 4.0 | 5.2 |
| 10 | 1.6 | 3.7 | 3.6 | 5.0 |
| 11 | 1.6 | 3.6 | 2.2 | 3.3 |
| 12 | 1.5 | 3.2 | 2.0 | 1.3 |
| 13 | 1.4 | 2.3 | 1.8 | |
| 14 | 1.4 | 2.3 | 1.4 | |
| 15 | 1.4 | 2.2 | | |
| 16 | 1.3 | 2.0 | | |
| 17 | 1.2 | 1.8 | | |
| 18 | 1.1 | 1.3 | | |
| 19 | 1.1 | 0.8 | | |
| 20 | 0.9 | | | |
| 21 | 0.8 | | | |
| 22 | 0.5 | | | |
| 23 | 0.4 | | | |
| 24 | 0.3 | | | |
| 25 | 0.2 | | | |

TABLE 15

Levels of Anti-EL-Selectin Antibody Expression in CHO Cells Transfected with pA-Gen-EL-Selectin

| pA-Gen-EL-Selectin clone# | 0 nM MTX | 20 nM MTX | 100 nM MTX | 500 nM MTX |
|---|---|---|---|---|
| 1 | 9.1 | 30.5 | 30.0 | 62.5 |
| 2 | 5.6 | 15.0 | 27.1 | 35.5 |
| 3 | 4.1 | 14.1 | 22.8 | 34.4 |
| 4 | 3.4 | 13.4 | 22.6 | 31.3 |
| 5 | 3.4 | 13.4 | 19.4 | 30.1 |
| 6 | 3.2 | 9.6 | 16.3 | 29.9 |
| 7 | 3.2 | 6.4 | 13.0 | 26.9 |
| 8 | 3.1 | 6.2 | 12.8 | 25.1 |
| 9 | 2.9 | 5.7 | 12.6 | 19.9 |
| 10 | 2.8 | 5.6 | 12.1 | 17.9 |
| 11 | 2.8 | 5.2 | 11.7 | 14.4 |
| 12 | 2.7 | 5.1 | 9.0 | 12.5 |
| 13 | 2.3 | 4.5 | 8.1 | 8.6 |
| 14 | 2.1 | 4.5 | 7.9 | 3.3 |
| 15 | 2.0 | 4.4 | 6.5 | 2.8 |
| 16 | 1.8 | 4.1 | 6.4 | 0.7 |
| 17 | 1.8 | 4.0 | 5.7 | |
| 18 | 1.6 | 3.9 | | |
| 19 | 1.6 | 3.8 | | |
| 20 | 1.4 | 3.4 | | |
| 21 | 1.3 | 3.4 | | |
| 22 | 1.1 | 3.3 | | |
| 23 | 1.1 | 2.7 | | |
| 24 | 1.1 | 2.6 | | |
| 25 | 1.0 | 2.6 | | |
| 26 | 1.0 | 2.4 | | |
| 27 | 0.9 | 2.3 | | |
| 28 | 0.9 | 2.1 | | |
| 29 | 0.8 | | | |
| 30 | 0.8 | | | |
| 31 | 0.7 | | | |
| 32 | 0.6 | | | |
| 33 | 0.2 | | | |
| 34 | 0.1 | | | |

Example 8

Enhancement of Expression of Anti-IL-13 Antibody

This study shows rEVE-mediated enhancement of expression of a humanized anti-IL-13 antibody in stably transfected mammalian cells in culture compared to cells transfected with the expression lacking rEVE.

DNA molecules encoding the heavy and light chains of a humanized anti-IL-13 monoclonal antibody, which has the human IgGγ1 isotype, (see, U.S. Ser. No. 11/899,819, incorporated herein by reference) were inserted into expression vector plasmid pBJ, a DHFR-MTX amplifiable expression plasmid, using standard methods to yield the expression plasmid pBJ-13C5.5 (parent expression plasmid). A rEVE polynucleotide comprising the ARM2 sequence (SEQ ID NO:2) was then inserted to plasmid pBJ-13C5.5 to yield the rEVE-containing expression plasmid pA2-13C5.5 (ARM2 rEVE expression plasmid).

CHO cells were transfected with either parent expression plasmid pBJ-13C5.5 or ARM2-containing rEVE expression plasmid pA2-13C5.5 following the general transfection protocol described in the previous examples to obtain stable transfectant CHO cells. At 24 hours after transfection, cells from each transfection were seeded into forty-eight (48) 96-well culture plates (200 cells/well). The culture media of individual wells were screened by ELISA for expression of human IgG. Optical densities were slightly higher in cultures (wells) of cells transfected with the ARM2 rEVE expression plasmid than for cells transfected with the parent expression plasmid. An average of 74 colonies (wells) per culture plate survived the selection process when cells were transfected with ARM2 rEVE plasmid pA2-13C5.5 compared to an average of 68 colonies per plate for cells transfected with the parent plasmid pBJ-13C5.5. Fifteen (15) stably transfected clones from each transfection were then subjected to DHFR-methotrexate (MTX) amplification.

Prior to amplification, the average level of expression of anti-IL-13 antibody obtained from ARM2 rEVE plasmid transfectant clones was two-fold higher than the average level of expression from the parent plasmid transfectant clones. Antibody expression was then amplified by either of two protocols. Using the basic protocol for DHFR-MTX amplification as described in Example 2, above, clones were first subjected to selection at a concentration of 20 nM MTX, followed by further selection at 100 nM MTX. In another amplification protocol, clones were selected directly at 100 nM MTX without an intervening selection at an intermediate MTX concentration. Table 16, below, shows the average level of production of anti-IL-13 antibody in cultures of the top three producing clones from each transfection after two passages in media containing the indicated level of amplification (concentration of methotrexate, "MTX").

Example 9

Effect of ARM1 and ARM2 rEVE Polynucleotide Molecules on Expression of Adalimumab in a Transient Expression System This study was designed to determine whether rEVE polynucleotide molecules will enhance levels of expression of recombinant proteins in a transient expression system.

HEK 293 cells were transfected with expression plasmid vectors pA205, pA205Genomic, pA205A1, pA205A2, pA205A2-Spec-trunc, and pA205A2-Swa-trunc. HEK293 cells cultured in Freestyle 293 Expression Medium (GIBCO®, Invitrogen, Carlsbad, Calif.) were transfected with plasmid DNAs complexed with polyethylenimine according to published conditions (Durocher et al., *Nucleic Acids Res.*, 30: E9). No selection for vector integration was performed. Cells were cultured for seven days after transfection and aliquots of culture supernatant were tested for adalimumab concentration as described above. The results of three transfections are shown in Table 17. The levels of expression were run in triplicate for the third transfection.

TABLE 17

Level* of Adalimumab Expression in Transfected HEK 293 Cells

| Transfection | pA205 | pA205 Genomic | pA205A1 | pA205A2 | pA205A2-Spe-trunc | pA205A2-Swa-trunc |
|---|---|---|---|---|---|---|
| 1 | 2.1 | 5.4 | 5.4 | 3.3 | | |
| 2 | 5.3 | 20.3 | 20.3 | 9.9 | | |
| 3 | 4.3 | 11.9 | 11.9 | 10.2 | 2.2 | 1.2 |
|   | 4.1 | 15.7 | 15.7 |      | 2.3 | 1.3 |
|   | 3.0 | 14.2 | 14.2 |      | 2.3 | 1.0 |

*µg/ml of adalimumab

TABLE 16

Level of Humanized Anti-IL-13 Antibody in Transfected CHO Cells

| Expression Vector | 0 nM MTX | 20 nM MTX | 100 nM MTX |
|---|---|---|---|
| pBJ-13C5.5 | 2.63 µg/ml | 2.00 µg/ml | 3.04 µg/ml |
| pBJ-13C5.5 | 2.63 µg/ml | N.A. | 1.72 µg/ml |
| pA2-13C5.5 | 4.35 µg/ml | 5.85 µg/ml | 14.94 µg/ml |
| pA2-13C5.5 | 4.35 µg/ml | N.A. | 14.33 µg/ml |

N.A. = not applicable, not part of amplification protocol

The data in Table 16 clearly show that the ARM2 rEVE enhanced the level of expression of humanized anti-IL-13 antibody by approximately 3-fold to 5-fold compared to the level of expression obtained from transfectants carrying the parent expression plasmid lacking the ARM2 rEVE DNA. In addition, one subclone of an ARM2 rEVE expression plasmid transfectant expressed the humanized anti-IL-13 antibody at a level as high 95 µg/ml and a specific productivity of 21.74 pg/cell/day when grown at an amplification level of 100 nM MTX.

Amplified levels of expression of anti-IL-13 antibody by clones transfected with the ARM2 rEVE expression plasmid were readily maintained for at least three weeks when grown under MTX selection.

The results in Table 17 show that ARM1 and ARM2 sequences can enhance the level of expression of adalimumab in HEK 293 cells when present separately on an expression plasmid vector (pA205A1, pA205A2) or in combination (pA205Genomic). ARM1 conferred a greater level of enhancement of adalimumab expression than ARM2 in this HEK 293 transient expression system. In contrast, ARM2 conferred a greater level of enhancement of expression of adalimumab than ARM1 in the CHO stable expression system (see, Example 3, above). As seen in the CHO stable expression system (Example 6, above), the enhancement effect of ARM2 was also clearly reduced in HEK 293 cells transfected with an expression plasmid vector carrying either the SpeI- or SwaI-truncated ARM2 sequence, including a lowering of expression below that seen in cells transfected with the pA205 control (no ARM sequence) plasmid expression vector.

All patents, applications, and publications cited in the above text are incorporated herein by reference.

Other variations and embodiments of the invention described herein will now be apparent to those skilled in the art, and all such variants and alternative embodiments of the invention are intended to be encompassed within the foregoing description and the claims that follow.

What is claimed is:

1. A yeast host cell comprising a recombinant vector, wherein the recombinant vector comprises a recombinant expression vector element (rEVE) polynucleotide molecule comprising a nucleotide sequence selected from the group consisting of:
the nucleotide base sequence of SEQ ID NO:1, the nucleotide base sequence of SEQ ID NO:2, a sequence complementary to any foregoing sequence, an expression-enhancing portion of any foregoing sequence, and combinations thereof;
and wherein the yeast host cell is selected from the group consisting of:
*Hansenula polymorpha, Kluyveromyces lactis, Pichia pastoris, Schizosaccharomyces pombe,* and *Yarrowia lipolytica.*

2. A nematode host cell comprising a recombinant vector, wherein the recombinant vector comprises a recombinant expression vector element (rEVE) polynucleotide molecule comprising a nucleotide sequence selected from the group consisting of:
the nucleotide base sequence of SEQ ID NO:1, the nucleotide base sequence of SEQ ID NO:2, a sequence complementary to any foregoing sequence, an expression-enhancing portion of any foregoing sequence, and combinations thereof;
and wherein the nematode host cell is *Caenorhabditis elegans.*

3. A prokaryotic host cell comprising a recombinant vector, wherein the recombinant vector comprises a recombinant expression vector element (rEVE) polynucleotide molecule comprising a nucleotide sequence selected from the group consisting of:
the nucleotide base sequence of SEQ ID NO:1, the nucleotide base sequence of SEQ ID NO:2, a sequence complementary to any foregoing sequence, an expression-enhancing portion of any foregoing sequence, and combinations thereof;
and wherein the prokaryotic host cell is selected from the group consisting of:
*Escherichia coli,* a serovar of *Salmonella enterica,* a *Shigella* species, *Wollinella succinogenes, Proteus vulgaris, Proteus mirabilis, Edwardsiella tarda, Citrobacter freundii,* a *Pasteurella* species, a *Haemophilus* species, a *Pseudomonas* species, a *Bacillus* species, a *Staphyloccocus* species, and a *Streptococcus* species.

4. A method of producing a recombinant protein of interest comprising:
inserting into a host cell a recombinant expression vector wherein the recombinant expression vector comprises:
one or more genes encoding the recombinant protein of interest; and
a nucleotide base sequence selected from the group consisting of: the nucleotide base sequence of SEQ ID NO:1, the nucleotide base sequence of SEQ ID NO:2, a sequence complementary to any foregoing sequence, an expression-enhancing portion of any foregoing sequence, and combinations thereof;
and
culturing the host cell under conditions promoting expression of the recombinant protein of interest.

5. The method according to claim 4, wherein said recombinant protein of interest is selected from the group consisting of a soluble protein, a membrane protein, a structural protein, a ribosomal protein, an enzyme, a zymogen, an antibody molecule, a cell surface receptor protein, a transcription regulatory protein, a translation regulatory protein, a chromatin protein, a hormone, a cell cycle regulatory protein, a G protein, a neuroactive peptide, an immunoregulatory protein, a blood component protein, an ion gate protein, a heat shock protein, a dihydrofolate reductase (DHFR), an antibiotic resistance protein, a functional fragment of any of the preceding proteins, an epitope-containing fragment of any of the preceding proteins, and combinations thereof.

6. The method according to claim 5, wherein the antibody molecule is selected from the group consisting of an antibody to an immunoregulatory protein, an antibody to a selectin, an antibody to a cell surface receptor, and a dual variable domain immunoglobulin (DVD-Ig) molecule.

7. The method according to claim 6, wherein the antibody to an immunoregulatory protein is an anti-IL-13 antibody or an anti-TNF-α antibody.

8. The method according to claim 7, wherein the anti-TNF-α antibody is adalimumab.

9. The method according to claim 6, wherein the antibody molecule is a dual variable domain immunoglobulin (DVD-Ig) molecule.

10. The method according to any one of claims 4-9, wherein the recombinant expression vector comprises at least one copy of a gene encoding a dihydrofolate reductase.

11. The method according to any one of claims 4-9, wherein the host cell is selected from the group consisting of: a Chinese Hamster Ovary (CHO) cell, a COS cell, a Vero cell, an SP2/0 cell, an NS/0 myeloma cell, a human embryonic kidney (HEK 293) cell, a baby hamster kidney (BHK) cell, a HeLa cell, a human B cell, a CV-1/EBNA cell, an L cell, a 3T3 cell, an HEPG2 cell, a PerC6 cell, and an MDCK cell.

12. The method according to claim 11, wherein the recombinant expression vector comprises at least one copy of a gene encoding a dihydrofolate reductase.

* * * * *

SEQUENCE LISTING

<160> NUMBER OF SEQ ID NOS: 18

<210> SEQ ID NO 1
<211> LENGTH: 2329
<212> TYPE: DNA
<213> ORGANISM: Cricetulus griseus

<400> SEQUENCE: 1

```
aattgaattc gttcccttta gtgagggtta attccgcggc cgcgtcgaca gctctagagg      60
gagtgccagg ataggctcca aagctacaca gagaatccct gtttcaaaaa accaaaaaaa     120
aaaaaataaa aaataaaaaa taaaaagtag ggtacagatc taaatagaca attctcaata     180
gaggaatcta aaatgcctga agacaaata agaaagtgtt caacatcctt agccatcagg      240
gaaatgcaaa tcaaaacaac tctgagatac tatcttactc ctgtcataat ggccaaattc     300
aaaaacacta atgacagttc atgttggaga gaatgtggag aaagaggagc acttctccac     360
tgctggtggg agtgccaact tggacagcca cttggaaat cagtatggct actcctcaag      420
aaaatggaaa tcagtttacc acaagatcca gcaattccac tcaggcatat acccaaaaga    480
accgcattca tacaagcaat atctgttcaa cgatgttcat agcagctcta tttgtaacag    540
ccagaaactg gaagcagcct agttgcacct caaccaaaga aatggataga gaaatatgg     600
tacatttatg caatggagta ctactcagcg gaaaagtaca atggaatctt gaaatttgca    660
agaaaatgga tggaactaga agaaaccttt ctgagcaagg taactcaatc acaaaaagac    720
aaacatgata tgtaatcact catatgtgga ttttagacac agtgtaaagg attaccagcc    780
tacaatccac actgccaaag aacctaataa acaaggagga ccctaaggga gacatacatg    840
gtcccctgga gatggggaat gggtcaagat atgctgagca aagtgggaac atgggaagag    900
ggggaagga gctaggaaat tgagaaaggg agaaaaggag ggatgcagag gacataaggg      960
agcagaaaca ttgactcagg gaatgaatcg aagataacaa gccatggaga tatcataata    1020
gagggagaca ttttgggtat acagagaaat caggcacttg ggaaatgtct ggaaatctac    1080
aaagtataac accaggtaac aatctaagca acagaggaga ggctaccta aatgtcctac    1140
cctgatagtg agattgatga ctaacttata tgccatgtta tagccttcat ccagcagctg    1200
gtggaagtag aagcagacac ccataactaa tcacggaact gaactggaac ccagattcag    1260
agaaggatga gtgaagggca cagaggtcca gaccaggctg gtgaaaccca caaaaacagt    1320
tgaactgaat atcggtgaac tcttgctccc cagactgata gctggaatac cagcatggga    1380
ctgatccaga ctccaggaac atgagttcct gtgaggaaac ctcggaaatc taagggacct    1440
cctgtagaag ttcagtactt atccctagca taggtgtgga ctgagggagc ccattccata    1500
tagaggaata ctctctggag ccaacacaca tgggggtggg cataggccct ttcccaaagc    1560
atacaataga ctcggatgac accctatgga aggcctcatc atccaggggg agcagaaagg    1620
atatgtgata gacagggttt cagttgggag ccgggtagtg ggagggaga attggtggaa     1680
gaaggaaacc gggattgtca tgtaaatcaa tgctgtttct aattcaaata agaaagttga    1740
aaaaaaagaa aactgatact tattgcacca tgtaatgtta tgaaatggca tttgctgtta    1800
agatgagcag tctatctgct aatctcccta gctggcttgt gaacttgtta tatggacaaa    1860
gctggtctca aattcaaaga tatttgcgta tgtctgtctc ctgagtgttg agagtacaag    1920
tatgtaccac caatcccttt gattatacaa ttacatttga aaacagtttg agatttaatt    1980
ataactatgc aatcaattca aaataataaa tttaaatctc atatttgtct ttaggtggaa    2040
```

```
atctgttaat atacatcatg attatatatt ttaatttatt atatgttttc taggacaaaa    2100
tatactaaaa tgaaatctaa ggctctaaac atacaaaact gtatgcatag atacatcacg    2160
atcatataat ttccatgaca tgctattcgg gaatataatg atctacctgc agtaatgatt    2220
aatttggaaa tgctgaatac aactgcttct cttttgaaaa tacaaattcc ttacatttgt    2280
aatctattta attttaaagg ttgtaccccc gaaagtagtg aattcttaa                2329

<210> SEQ ID NO 2
<211> LENGTH: 2422
<212> TYPE: DNA
<213> ORGANISM: Cricetulus griseus

<400> SEQUENCE: 2
aagaatatgc tcaatgtaat acccatggca ggcattcaat gtttgtctgt cttcatattg      60
aagataaaca gatgtatatc atatacaaaa atatttaatg tgaagttgtc catgtgttca     120
ggatctatat actttcaaaa atcttttttcc atattctttt cttaatcctc ctgaagtgta    180
gaccattata ctggaaaacc gtcactattg tacaggatag gagcctttga ctctgagagg    240
atcccataca ttgattgtat tttcaaatat attttggctg cttttctcca tgtgatattt    300
ggcaatctgg agaggcattt gctcctggaa atttatcaat gttgacaatg ttgtttacat    360
gttttaagta actattttgc taccaaggaa actgcttcac tcccttttcac atataaaact   420 cataaaatat tgaaaggctc caataagttt aaatcattct gtattgctca tggagattta    480
aatttcagtg ctaattttt attagcactt taatttagaa ggcaccaggt ttctacaaga     540
tttaaaatta ttggagcatt tcaaaatttt ataagctttc cagtaaggtt gtggctatga    600
ttctttgctt gtaaagtaaa gtgcaattta agttaatttt aaataattta actgctgcag    660 acatttttagg agaattgttt gtatttcaaa ctgaaattca gggtagacaa ttagaataat   720
tttacaaaga ggaaatattt ttctaataat aaattagtaa ctctaactta tattaaaatt    780
taagtcctca ttgctttcaa tattttaaca accctattgt attattttttc ttataaatat   840 ttgaatttat aatgatcaaa gaatttcttt gatacaagtg tctaaatgat taccatcaaa    900
ctgttggtag gagcttgtta tatatgtgtt ttaccttatg ttttttgata cttcatttgt     960
tactgtactg tgatcgagtt aattccctac tgaaactaaa aatgctatca catagttta    1020 gcatcatctg ttggggaaat ggctattta actactctga gatgagaaat tcaacaccat    1080
tcactaacaa tatagggaaa ctagtgttgg tagattgttg agtgcttata catatatctt    1140
gtcccatggt taactataag ttggtgtctg ttgctgccac ccagtatgga aacacattat    1200 gttttttcctt ttttttttt tatagccatg agaaagacca aaattctata cttgaaaaac   1260
cgtttatatt gaatgtgtat tcctttcacg tccaccttag attcaactcc taagtcaatt    1320
tatggtaaag catagatcat ctgcttgaca acagtttgga tgatgatctt ggaaaaaatg   1380
ccttattata tgatacaatg gaattaatga tatgagctga ataaatatat caatattcaa   1440
atgacatact aatatttatg tctaagagaa tgtgttcaaa gtagatgaaa gtgccttcac    1500
ttgaaaattc atctgagtta aaacagatag ttgcttcggt tttagttatt tcagaggtat    1560
tcaagttgac aactaagaat agccgtcaca gatacatatc aattatggac ccaaattcta    1620
ttgaatgtca gctacatatt cttatagaaa ataggaacct agatgaggcc gtgttcttgg    1680
aatgaatttt caacacattg tatgagggtt ttattgtggt tttggttgtt gttttacttt    1740
cctttttttc catagacaaa tttgtcccat gtacccacaa ggtgaccagt ggtgacaagc    1800
ctactccagg agtcctggtg aataaagatt atacaagata gtagagactc atcaaaacaa    1860
```

-continued

```
taagaaaaag agaatacata gggcagaaat ttctcatttt ctcagctatg gtatcctatt   1920
tcactcttgt actattctac tcactagaag tcagtgacta ccataactca gtggctgtgc   1980
cctagatcaa aggaaacatt atttcaaggc atgaatgtca gccacacctt catagtgggt   2040
tacttttaat ttgtttagta agaatagaca ccctactttg gttaggaaac ataaacttac   2100
aagacattca ttggtttttc tttactaaat taaatcatta agaaaatcgt aattatcaga   2160
gtttaaatgg catgaaacat agaaatactc atttgctgcc ctgatttatt ttcccaagaa   2220
tattttcaat gtcttctttg gaagctcctt ggtaaatgca cttcttcttca ctcatttatg   2280 aggtctgtgc acatcacagt caataaaggc ctgcagtatt gaatcagcca tacagacata   2340
attcataaca tttttctatt tctcatgaat caaatattgt tattgctgta cataaaataa   2400
tgaatcaaag tataggtcta ga                                             2422
```

<210> SEQ ID NO 3
<211> LENGTH: 9
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (7)..(7)
<223> OTHER INFORMATION: y is t or c

<400> SEQUENCE: 3

```
aataaayaa                                                               9
```

<210> SEQ ID NO 4
<211> LENGTH: 10
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (5)..(5)
<223> OTHER INFORMATION: w is a or t
<220> FEATURE:
<221> NAME/KEY: misc_feature
<222> LOCATION: (8)..(8)
<223> OTHER INFORMATION: w is a or t

<400> SEQUENCE: 4

```
ttwtwttwtt                                                              10
```

<210> SEQ ID NO 5
<211> LENGTH: 21
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (5)..(7)
<223> OTHER INFORMATION: w is a or t
<220> FEATURE:
<221> NAME/KEY: misc_feature
<222> LOCATION: (8)..(9)
<223> OTHER INFORMATION: n is a, t, g or c
<220> FEATURE:

```
<221> NAME/KEY: misc_feature
<222> LOCATION: (11)..(12)
<223> OTHER INFORMATION: w is a or t
<220> FEATURE:
<221> NAME/KEY: misc_feature
<222> LOCATION: (13)..(13)
<223> OTHER INFORMATION: r is g or a
<220> FEATURE:
<221> NAME/KEY: misc_feature
<222> LOCATION: (17)..(18)
<223> OTHER INFORMATION: n is a, t, g or c
<220> FEATURE:
<221> NAME/KEY: misc_feature
<222> LOCATION: (19)..(20)
<223> OTHER INFORMATION: w is a or t

<400> SEQUENCE: 5
tawawwwnna wwrtaannww g                                        21

<210> SEQ ID NO 6
<211> LENGTH: 11
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (7)..(7)
<223> OTHER INFORMATION: r is g or a
<220> FEATURE:
<221> NAME/KEY: misc_feature
<222> LOCATION: (11)..(11)
<223> OTHER INFORMATION: w is a or t

<400> SEQUENCE: 6
wtttatrttt w                                                   11

<210> SEQ ID NO 7
<211> LENGTH: 9
<212> TYPE: DNA
<213> ORGANISM: unknown
<220> FEATURE:
<223> OTHER INFORMATION: MAR element

<400> SEQUENCE: 7 aatatattt                                                       9

<210> SEQ ID NO 8
<211> LENGTH: 26
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (5)..(11)
<223> OTHER INFORMATION: n is a, t, g, or c
<220> FEATURE:
<221> NAME/KEY: misc_feature
<222> LOCATION: (16)..(22)
<223> OTHER INFORMATION: n is a, t, g, or c

<400> SEQUENCE: 8 aaaannnnn naaaannnnn nnaaaa                                    26

<210> SEQ ID NO 9
<211> LENGTH: 6
<212> TYPE: DNA
```

```
<213> ORGANISM: unknown
<220> FEATURE:
<223> OTHER INFORMATION: MAR element

<400> SEQUENCE: 9 tttaaa                                                                    6

<210> SEQ ID NO 10
<211> LENGTH: 20
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (1)..(20)
<223> OTHER INFORMATION: w is a or t

<400> SEQUENCE: 10 wwwwwwwww wwwwwwwww                                                      20

<210> SEQ ID NO 11
<211> LENGTH: 12
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(5)
<223> OTHER INFORMATION: n is a, t, g, or c
<220> FEATURE:
<221> NAME/KEY: misc_feature
<222> LOCATION: (8)..(10)
<223> OTHER INFORMATION: n is a, t, g, or c

<400> SEQUENCE: 11
tannntgnnn ca                                                            12

<210> SEQ ID NO 12
<211> LENGTH: 12
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(5)
<223> OTHER INFORMATION: n is a, t, g, or c
<220> FEATURE:
<221> NAME/KEY: misc_feature
<222> LOCATION: (8)..(10)
<223> OTHER INFORMATION: n is a, t, g, or c

<400> SEQUENCE: 12
tannncannn tg                                                            12

<210> SEQ ID NO 13
<211> LENGTH: 12
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(5)
<223> OTHER INFORMATION: n is a, t, g, or c
<220> FEATURE:
<221> NAME/KEY: misc_feature
<222> LOCATION: (8)..(10)
<223> OTHER INFORMATION: n is a, t, g, or c
```

```
<400> SEQUENCE: 13
tgnnntannn ca                                                      12

<210> SEQ ID NO 14
<211> LENGTH: 12
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(5)
<223> OTHER INFORMATION: n is a, t, g, or c
<220> FEATURE:
<221> NAME/KEY: misc_feature
<222> LOCATION: (8)..(10)
<223> OTHER INFORMATION: n is a, t, g, or c

<400> SEQUENCE: 14
cannntannn tg                                                      12

<210> SEQ ID NO 15
<211> LENGTH: 15
<212> TYPE: DNA
<213> ORGANISM: unknown
<220> FEATURE:
<223> OTHER INFORMATION: MAR element
<220> FEATURE:
<221> NAME/KEY: misc_feature
<222> LOCATION: (3)..(3)
<223> OTHER INFORMATION: n is a, t, g, or c
<220> FEATURE:
<221> NAME/KEY: misc_feature
<222> LOCATION: (4)..(4)
<223> OTHER INFORMATION: w is a or t
<220> FEATURE:
<221> NAME/KEY: misc_feature
<222> LOCATION: (6)..(6)
<223> OTHER INFORMATION: y is t or c
<220> FEATURE:
<221> NAME/KEY: misc_feature
<222> LOCATION: (10)..(10)
<223> OTHER INFORMATION: n is a, t, g, or c
<220> FEATURE:
<221> NAME/KEY: misc_feature
<222> LOCATION: (13)..(14)
<223> OTHER INFORMATION: n is a, t, g, or c
<220> FEATURE:
<221> NAME/KEY: misc_feature
<222> LOCATION: (15)..(15)
<223> OTHER INFORMATION: r is g or a

<400> SEQUENCE: 15
gtnwayattn atnnr                                                   15

<210> SEQ ID NO 16
<211> LENGTH: 7
<212> TYPE: DNA
<213> ORGANISM: unknown
<220> FEATURE:
<223> OTHER INFORMATION: MAR element

<400> SEQUENCE: 16 caaaaca                                                             7

<210> SEQ ID NO 17
<211> LENGTH: 6
<212> TYPE: DNA
<213> ORGANISM: unknown
<220> FEATURE:
<223> OTHER INFORMATION: MAR element
```

```
<400> SEQUENCE: 17 aatatt                                                              6

<210> SEQ ID NO 18
<211> LENGTH: 8
<212> TYPE: DNA
<213> ORGANISM: unknown
<220> FEATURE:
<223> OTHER INFORMATION: MAR sequence motifs

<400> SEQUENCE: 18 aatatatt                                                            8
```